United States Patent
Xing et al.

(10) Patent No.: US 11,911,356 B2
(45) Date of Patent: Feb. 27, 2024

(54) REGULATION OF MUTANT TERT BY BRAF V600E/MAP KINASE PATHWAY THROUGH FOS/GABP IN HUMAN CANCER

(71) Applicant: THE JOHNS HOPKINS UNIVERSITY, Baltimore, MD (US)

(72) Inventors: Michael Mingzhao Xing, Clarkesville, MD (US); Rengyun Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/956,675

(22) PCT Filed: Dec. 22, 2018

(86) PCT No.: PCT/US2018/067419
§ 371 (c)(1),
(2) Date: Jun. 22, 2020

(87) PCT Pub. No.: WO2019/126816
PCT Pub. Date: Jun. 27, 2019

(65) Prior Publication Data
US 2020/0323805 A1    Oct. 15, 2020

Related U.S. Application Data

(60) Provisional application No. 62/609,587, filed on Dec. 22, 2017.

(51) Int. Cl.
| | |
|---|---|
| *A61K 31/196* | (2006.01) |
| *A61K 31/4184* | (2006.01) |
| *A61K 31/423* | (2006.01) |
| *A61K 31/437* | (2006.01) |
| *A61K 31/4545* | (2006.01) |
| *A61K 31/506* | (2006.01) |
| *A61K 31/519* | (2006.01) |
| *A61K 45/06* | (2006.01) |

(52) U.S. Cl.
CPC ........ *A61K 31/196* (2013.01); *A61K 31/4184* (2013.01); *A61K 31/423* (2013.01); *A61K 31/437* (2013.01); *A61K 31/4545* (2013.01); *A61K 31/506* (2013.01); *A61K 31/519* (2013.01); *A61K 45/06* (2013.01)

(58) Field of Classification Search
CPC ........ A61K 8/35; A61K 31/42; A61K 31/421; A61P 35/00
See application file for complete search history.

(56) References Cited

U.S. PATENT DOCUMENTS

| | | |
|---|---|---|
| 2005/0095226 A1 | 5/2005 | Gjerset |
| 2015/0320754 A1 | 11/2015 | Kutok et al. |
| 2016/0040250 A1 | 2/2016 | Xing |
| 2017/0022572 A1 | 1/2017 | Xing |
| 2017/0079979 A1 | 3/2017 | Azam et al. |

FOREIGN PATENT DOCUMENTS

| | | | | |
|---|---|---|---|---|
| CN | 102319234 A | * | 1/2012 | |
| WO | 2010/118419 A4 | | 10/2010 | |
| WO | WO-2012145575 A2 | * | 10/2012 | ........... A61K 31/045 |
| WO | WO-2014160834 A1 | * | 10/2014 | ........... C12Q 1/6886 |
| WO | WO-2015153808 A1 | * | 10/2015 | ......... A61K 31/4184 |
| WO | WO-2015155218 A1 | * | 10/2015 | ...... A61K 39/001102 |
| WO | 2015/183826 A1 | | 12/2015 | |
| WO | 2017/085351 A1 | | 5/2017 | |

OTHER PUBLICATIONS

Zhao (Oncology Reports vol. 35 pp. 1065-1074 published 2016). (Year: 2016).*
Kamide (Cancer Science vol. 107 pp. 666-673 published Feb. 2016). (Year: 2016).*
Liu (Endocr Relat Cancer vol. 20 pp. 603-610 published 2013) (Year: 2013).*
Low, et al., Telomerase: central regulator of all of the hallmarks of cancer. Trends Biochem Sci. Sep. 2013;38(9):426-34.
Horn, et al., TERT promoter mutations in familial and sporadic melanoma. Science. Feb. 22, 2013;339(6122):959-61.
Huang, et al., Highly recurrent TERT promoter mutations in human melanoma. Science. Feb. 22, 2013;339(6122):957-9.
Killela, et al., TERT promoter mutations occur frequently in gliomas and a subset of tumors derived from cells with low rates of self-renewal. Proc Natl Acad Sci U S A. Apr. 9, 2013;110(15):6021-6.
Liu, et al., TERT promoter mutations in thyroid cancer. Endocr Relat Cancer. Mar. 2016;23(3):R143-55.
Liu, et al., Highly prevalent TERT promoter mutations in aggressive thyroid cancers. Endocr Relat Cancer. Jul. 12, 2013;20(4):603-10.
Borah, et al., TERT promoter mutations and telomerase reactivation in urothelial cancer. Science. Feb. 27, 2015;347(6225):1006-1010.
Chiba, et al., Cancer-associated TERT promoter mutations abrogate telomerase silencing. Elife. Jul. 21, 2015;4.
Heidenreich, et al., Telomerase reverse transcriptase promoter mutations in primary cutaneous melanoma. Nat Commun. Feb. 26, 2014;5:3401.
Li, et al., The C228T mutation of TERT promoter frequently occurs in bladder cancer stem cells and contributes to tumorigenesis of bladder cancer. Oncotarget. Aug. 14, 2015;6(23):19542-51.

(Continued)

*Primary Examiner* — Theodore R. Howell
*Assistant Examiner* — George W Kosturko
(74) *Attorney, Agent, or Firm* — Johns Hopkins Technology Ventures

(57) ABSTRACT

The present invention relates to the field of cancer. More specifically, the present invention provides methods and compositions useful for the treatment of cancer characterized by TERT and BRAF mutations. In a specific embodiment, a method for treating a mutant telomerase reverse trancriptase (TERT) enzyme-associated cancer in a subject comprises the step of administering to the subject an anti-cancer agent that inhibits one or more of FOS, GABPB, the formation of the GABPA-GABPB complex or the binding of the GABPA-GABPB complex to a mutant TERT promoter.

14 Claims, 23 Drawing Sheets

Specification includes a Sequence Listing.

(56) References Cited

OTHER PUBLICATIONS

Davies, et al., Mutations of the BRAF gene in human cancer. Nature. Jun. 27, 2002;417(6892):949-54.
Xing, BRAF mutation in thyroid cancer. Endocr Relat Cancer. Jun. 2005;12(2):245-62.
Xing, et al., Association between BRAF V600E mutation and recurrence of papillary thyroid cancer. J Clin Oncol. Jan. 1, 2015;33(1):42-50.
Xing, et al., Association between BRAF V600E mutation and mortality in patients with papillary thyroid cancer. JAMA. Apr. 10, 2013;309(14):1493-501.
Safaee Ardekani, et al., The prognostic value of BRAF mutation in colorectal cancer and melanoma: a systematic review and metaanalysis. PLoS One. 2012;7(10):e47054.
Thomas, et al., Association Between NRAS and BRAF Mutational Status and Melanoma-Specific Survival Among Patients With Higher-Risk Primary Melanoma. JAMA Oncol. Jun. 2015;1(3):359-68.
Dahiya, et al., BRAF(V600E) mutation is a negative prognosticator in pediatric ganglioglioma. Acta Neuropathol. Jun. 2013;125(6):901-10.
Summers, et al., BRAF and NRAS Locus-Specific Variants Have Different Outcomes on Survival to Colorectal Cancer. Clin Cancer Res. Jun. 1, 2017;23(11):2742-2749.
Griewank, et al., TERT promoter mutation status as an independent prognostic factor in cutaneous melanoma. J Natl Cancer Inst. Sep. 13, 2014;106(9).
Eckel-Passow, et al., Glioma Groups Based on 1p/19q, IDH, and TERT Promoter Mutations in Tumors. N Engl J Med. Jun. 25, 2015;372(26):2499-508.
Rachakonda, et al., TERT promoter mutations in bladder cancer affect patient survival and disease recurrence through modification by a common polymorphism. Proc Natl Acad Sci U S A. Oct. 22, 2013;110(43):17426-31.
Macerola, et al., Coexistence of TERT promoter and BRAF mutations in cutaneous melanoma is associated with more clinicopathological features of aggressiveness. Virchows Arch. Aug. 2015;467(2):177-84.
Nagore, et al., TERT promoter mutations in melanoma survival. Int J Cancer. Jul. 1, 2016;139(1):75-84.
Liu, et al., Mortality Risk Stratification by Combining Braf V600E and TERT Promoter Mutations in Papillary Thyroid Cancer: Genetic Duet of BRAF and TERT Promoter Mutations in Thyroid Cancer Mortality. JAMA Oncol. 2017;3(2):202-208.
Shen, et al., A six-genotype genetic prognostic model for papillary thyroid cancer. Endocr Relat Cancer. Jan. 2017;24(1):41-52.
Song, et al., Prognostic effects of TERT promoter mutations are enhanced by coexistence with BRAF or RAS mutations and strengthen the risk prediction by the ATA or TNM staging system in differentiated thyroid cancer patients. Cancer. May 1, 2016;122(9):1370-9.
Xing, et al., BRAF V600E and TERT promoter mutations cooperatively identify the most aggressive papillary thyroid cancer with highest recurrence. J Clin Oncol. Sep. 1, 2014;32(25):2718-26.
Halaban, et al., PLX4032, a selective BRAF(V600E) kinase inhibitor, activates the ERK pathway and enhances cell migration and proliferation of BRAF melanoma cells. Pigment Cell Melanoma Res. Apr. 2010;23(2):190-200.
Joseph, et al., The RAF inhibitor PLX4032 inhibits ERK signaling and tumor cell proliferation in a V600E BRAF-selective manner. Proc Natl Acad Sci U S A. Aug. 17, 2010;107(33):14903-8.
Wu, et al., Direct activation of TERT transcription by c-MYC. Nat Genet. Feb. 1999;21(2):220-4.
Bell, et al., Cancer. The transcription factor GABP selectively binds and activates the mutant TERT promoter in cancer. Science. May 29, 2015;348(6238):1036-9.
Stern, et al., Mutation of the TERT promoter, switch to active chromatin, and monoallelic TERT expression in multiple cancers. Genes Dev. Nov. 1, 2015;29(21):2219-24.
Lamarco, et al., Identification of Ets- and notch-related subunits in GA binding protein. Science. Aug. 16, 1991;253 (5021):789-92.
Sawada, et al., Transcriptional activation through the tetrameric complex formation of E4TF1 subunits. EMBO J. Mar. 15, 1994;13(6):1396-402.
Akincilar, et al., Long-Range Chromatin Interactions Drive Mutant TERT Promoter Activation. Cancer Discov. Nov. 2016;6(11):1276-1291.
Chen, et al., Phosphorylation of c-Fos at the Cterminus enhances its transforming activity. Oncogene. Apr. 4, 1996;12(7):1493-502.
Okazaki, et al., The Mos/MAP kinase pathway stabilizes c-Fos by phosphorylation and augments its transforming activity in NIH 3T3 cells. EMBO J. Oct. 16, 1995;14(20):5048-59.
Monje, et al., Phosphorylation of the carboxyl-terminal transactivation domain of c-Fos by extracellular signal-regulated kinase mediates the transcriptional activation of AP-1 and cellular transformation induced by platelet-derived growth factor. Mol Cell Biol. Oct. 2003;23(19):7030-43.
Ngeow, et al., TERT and BRAF in thyroid cancer: teaming up for trouble. J Clin Oncol. Sep. 1, 2014;32(25):2683-4.
Monje, et al., Regulation of the transcriptional activity of c-Fos by ERK. A novel role for the prolyl isomerase PIN1. J Biol Chem. Oct. 21, 2005;280(42):35081-4.
Li, et al., Activation of mutant TERT promoter by RAS-ERK signaling is a key step in malignant progression of BRAF-mutant human melanomas. Proc Natl Acad Sci U S A. Dec. 13, 2016;113(50):14402-14407.
Choi, et al., TERT promotes epithelial proliferation through transcriptional control of a Myc- and Wnt-related developmental program. PLOS Genet. Jan. 2008;4(1):e10.
Hrdlickova, et al., Alternatively spliced telomerase reverse transcriptase variants lacking telomerase activity stimulate cell proliferation. Mol Cell Biol. Nov. 2012;32(21):4283-96.
Artandi, et al., Constitutive telomerase expression promotes mammary carcinomas in aging mice. Proc Natl Acad Sci U S A. Jun. 11, 2002;99(12):8191-6.
Liu, et al., Genetic alterations in the phosphoinositide 3-kinase/Akt signaling pathway confer sensitivity of thyroid cancer cells to therapeutic targeting of Akt and mammalian target of rapamycin. Cancer Res. Sep. 15, 2009;69(18):7311-9.
Stewart, et al., Telomerase contributes to tumorigenesis by a telomere length-independent mechanism. Proc Natl Acad Sci U S A. Oct. 1, 2002;99(20):12606-11.
Maida, et al., An RNA-dependent RNA polymerase formed by TERT and the RMRP RNA. Nature. Sep. 10, 2009;461(7261):230-5.
Khattar, et al., Telomerase reverse transcriptase promotes cancer cell proliferation by augmenting tRNA expression. J Clin Invest. Oct. 3, 2016;126(10):4045-4060.
Koh, et al., Telomerase regulates MYC-driven oncogenesis independent of its reverse transcriptase activity. J Clin Invest. May 2015;125(5):2109-22.
Sun, J., et al., "Rapamycin inhibits ox-LDL-induced inflammation in human endothelial cells in vitro by inhibiting the mTORC2/PKC/c-Fos pathway" Acta Pharmacologica Sinica (2018) 39: 336-344.
Liu, et al., Activities of multiple cancer-related pathways are associated with BRAF mutation and predict the resistance to BRAF/MEK inhibitors in melanoma cells. Cell Cycle. 2014;13(2):208-19.
Xing, et al., BRAF mutation predicts a poorer clinical prognosis for papillary thyroid cancer. J Clin Endocrinol Metab. Dec. 2005;90(12):6373-9.
Livak, et al., Analysis of relative gene expression data using real-time quantitative PCR and the 2(-Delta Delta C(T)) Method. Methods. Dec. 2001;25(4):402-8.
Murugan, et al., Mutations in critical domains confer the human mTOR gene strong tumorigenicity. J Biol Chem. Mar. 1, 2013;288(9):6511-21.
Hou, et al., Genome-wide alterations in gene methylation by the BRAF V600E mutation in papillary thyroid cancer cells. Endocr Relat Cancer. Nov. 14, 2011;18(6):687-97.
Boehm, et al., Integrative genomic approaches identify IKBKE as a breast cancer oncogene. Cell. Jun. 15, 2007;129(6):1065-79.
Nelson, et al., Protocol for the fast chromatin immunoprecipitation (ChIP) method. Nat Protoc. 2006;1(1):179-85.

(56) References Cited

OTHER PUBLICATIONS

Liu, et al., BRAF V600E maintains proliferation, transformation, and tumorigenicity of BRAF-mutant papillary thyroid cancer cells. J Clin Endocrinol Metab. Jun. 2007;92(6):2264-71.
Tomayko, et al., Determination of subcutaneous tumor size in athymic (nude) mice. Cancer Chemother Pharmacol. 1989;24(3):148-54.
Genovese, et al., Abatacept for rheumatoid arthritis refractory to tumor necrosis factora inhibition. N Engl J Med. Sep. 15, 2005;353(11):1114-23.
Camps, et al., Blockade of PI3Kg suppresses joint inflammation and damage in mouse models of rheumatoid arthritis. Nat Med. Sep. 2005;11(9):936-43.
Rossi, et al., Cyclin-dependent kinase inhibitors enhance the resolution of inflammation by promoting inflammatory cell apoptosis. Nat Med. Sep. 2006;12(9):1056-64.
Scott, et al., Tumor necrosis factor inhibitors for rheumatoid arthritis. N Engl J Med. Aug. 17, 2006;355(7):704-12.
Hochberg, et al., The benefit/risk profile of TNF-blocking agents: findings of a consensus panel. Semin Arthritis Rheum. Jun. 2005;34(6):819-36.
Mancarella, et al., Good clinical response, remission, and predictors of remission in rheumatoid arthritis patients treated with tumor necrosis factor-alpha blockers: the GISEA study. J Rheumatol. Aug. 2007;34(8):1670-3.
Angel, et al., The role of Jun, Fos and the AP-1 complex in cell-proliferation and transformation. Biochim Biophys Acta. Dec. 10, 1991;1072(2-3):129-57.
Karin, et al., AP-1 function and regulation. Curr Opin Cell Biol. Apr. 1997;9(2):240-6.
Angel, et al., Phorbol ester-inducible genes contain a common cis element recognized by a TPA-modulated trans-acting factor. Cell. Jun. 19, 1987;49(6):729-39.
Schonthal, et al., Requirement for fos gene expression in the transcriptional activation of collagenase by other oncogenes and phorbol esters. Cell. Jul. 29, 1988;54(3):325-34.
Gutman, et al., The collagenase gene promoter contains a TPA and oncogene-responsive unit encompassing the PEA3 and AP-1 binding sites. EMBO J. Jul. 1990;9(7):2241-2246.
Shiozawa, et al., Destructive arthritis without lymphocyte infiltration in H2-c-fos transgenic mice. J Immunol. May 15, 1992;148(10):3100-4.
Kuroki, et al., Constitutive expression of c-fos gene inhibits type 1 collagen synthesis in transfected osteoblasts. Biochem Biophys Res Commun. Feb. 14, 1992;182(3):1389-94.
Lee, et al., Cadherin-11 in synovial lining formation and pathology in arthritis. Science. Feb. 16, 2007;315(5814):1006-10.
Shiozawa, et al., Studies on the contribution of c-fos/AP-1 to arthritic joint destruction. J Clin Invest. Mar. 15, 1997;99(6):1210-1216.
Koopman, The future of biologics in the treatment of rheumatoid arthritis. Semin Arthritis Rheum. Jun. 1994;23(6 Suppl 2):50-8.
Kawasaki, et al., Human wee1 kinase is directly transactivated by and increased in association with c-Fos/AP-1: rheumatoid synovial cells overexpressing these genes go into aberrant mitosis. Oncogene. Oct. 9, 2003;22(44):6839-44.
Sirum-Connolly, et al., Interleukin-1 or phorbol induction of the stromelysin promoter requires an element that cooperates with AP-1. Nucleic Acids Res. Jan. 25, 1991;19(2):335-341.
Hess, et al., AP-1 and Cbfa/Runt physically interact and regulate parathyroid hormone-dependent MMP13 expression in osteoblasts through a new osteoblast-specific element 2/ AP-1 composite element. J Biol Chem. Jun. 8, 2001;276(23):20029-38.
Sun, et al., Basic calcium phosphate crystals induce matrix metalloproteinase-1 through the Ras/mitogen-activated protein kinase/c-Fos/AP-1/metalloproteinase 1 pathway. J Biol Chem. Jan. 11, 2002;277(2):1544-52.
Whitmarsh, et al., Integration of MAP kinase signal transduction pathways at the serum response element. Science. Jul. 21, 1995;269(5222):403-7.

Dayer, The pivotal role of interleukin-1 in the clinical manifestations of rheumatoid arthritis. Rheumatology (Oxford). May 2003;42 Suppl 2:ii3-10.
Van Den Berg, Lessons from animal models of arthritis. Curr Rheumatol Rep. Jun. 2002;4(3):232-9.
Teitelbaum, RANKing c-Jun in osteoclast development. J Clin Invest. Aug. 16, 2004;114(4):463-465.
Kobayashi, et al., Tumor necrosis factor a stimulates osteoclast differentiation by a mechanism independent of the ODF/RANKL-RANK interaction. J Exp Med. Jan. 17, 2000;191(2):275-86.
Redlich, et al., Osteoclasts are essential for TNF-a-mediated joint destruction. J Clin Invest. Nov. 2002;110(10):1419-27.
Joosten, et al., IL-1ab blockade prevents cartilage and bone destruction in murine type II collagen-induced arthritis, whereas TNF-a blockade only ameliorates joint inflammation. J Immunol. Nov. 1, 1999;163(9):5049-55.
Probert, et al., The type I IL-1 receptor acts in series with TNF1 to induce arthritis in TNF-transgenic mice. Eur J Immunol. Jun. 1995;25(6):1794-7.
Horai, et al., Development of chronic inflammatory arthropathy resembling rheumatoid arthritis in IL-1 receptor antagonist-deficient mice. J Exp Med. Jan. 17, 2000;191(2):313-20.
Tsuchida, et al., Design, synthesis, and biological evaluation of new cyclic disulfide decapeptides that inhibit the binding of AP-1 to DNA. J Med Chem. Aug. 12, 2004;47(17):4239-46.
Tsuchida, et al., Discovery of nonpeptidic small-molecule AP-1 inhibitors: lead hopping based on 3D pharmacophore model. J Med Chem. Jan. 12, 2006;49(1):80-91.
Glover, et al., Crystal structure of the heterodimeric bZIP transcription factor c-Fos-c-Jun bound to DNA. Nature. Jan. 19, 1995;373(6511):257-61.
Matsuo, et al., Nuclear factor of activated T-cells (NFAT) rescues osteoclastogenesis in precursors lacking c-Fos. J Biol Chem. Jun. 18, 2004;279(25):26475-80.
Smolen, et al., Therapeutic strategies for rheumatoid arthritis. Nat Rev Drug Discov. Jun. 2003;2(6):473-88.
Mudgett, et al., Susceptibility of stromelysin 1-deficient mice to collageninduced arthritis and cartilage destruction. Arthritis Rheum. Jan. 1998;41(1):110-21.
Conway, et al., Inhibition of cartilage and bone destruction in adjuvant arthritis in the rat by a matrix metalloproteinase inhibitor. J Exp Med. Aug. 1, 1995;182(2):449-57.
Lewis, et al., Ro 32-3555, an orally active collagenase inhibitor, prevents cartilage breakdown in vitro and in vivo. Br J Pharmacol. Jun. 1997;121(3):540-6.
Kawabata, et al., Ameliorative effects of follistain-related protein/TSC-36/FSTL1 on joint inflammation in a mouse model of arthritis. Arthritis Rheum. Feb. 2004;50(2):660-8.
Shiozawa, et al., Morphologic observations in the early phase of the cartilage-pannus junction. Arthritis Rheum. Apr. 1983;26(4):472-8.
Han, et al., c-Jun N-terminal kinase is required for metalloproteinase expression and joint destruction in inflammatory arthritis. J Clin Invest. Jul. 2001;108(1):73-81.
Fahmy, et al., Suppression of vascular permeability and inflammation by targeting of the transcription factor c-Jun. Nat Biotechnol. Jul. 2006;24(7):856-63.
Siegel, et al., Cancer statistics, 2013. CA Cancer J Clin. Jan. 2013;63(1):11-30.
Ondrey, et al., Constitutive activation of transcription factors NF-jB, AP-1, and NF-IL6 in human head and neck squamous cell carcinoma cell lines that express pro-inflammatory and pro-angiogenic cytokines. Mol Carcinog. Oct. 1999;26(2):119-29.
De Sousa, et al., Immunolocalization of c-Fos and c-Jun in human oral mucosa and in oral squamous cell carcinoma. J Oral Pathol Med. Feb. 2002;31(2):78-81.
Mishra, et al., Transactivation and expression patterns of Jun and Fos/AP-1 super-family proteins in human oral cancer. Int J Cancer. Feb. 15, 2010;126(4):819-29.
Ozanne, et al., Transcription factors control invasion: AP-1 the first among equals. Oncogene. Jan. 4, 2007;26(1):1-10.
Shaulian, et al., AP-1 in cell proliferation and survival. Oncogene. Apr. 30, 2001;20(19):2390-400.

(56) References Cited

OTHER PUBLICATIONS

Aikawa, et al., Treatment of arthritis with a selective inhibitor of c-Fos/activator protein-1. Nat Biotechnol. Jul. 2008;26(7):817-23.
Yokoi, et al., Establishment and characterization of OSC-19 cell line in serum- and protein-free culture. Tumor Res. 1989;24:57-73.
Matsui, et al., Isolation of a highly metastatic cell line to lymph node in human oral squamous cell carcinoma by orthotopic implantation in nude mice. Oral Oncol. Jul. 1998;34(4):253-6.
Mook, et al., In situ localization of gelatinolytic activity in the extracellular matrix of metastases of colon cancer in rat liver using quenched fluorogenic DQ-gelatin. J Histochem Cytochem. Jun. 2003;51(6):821-9.
Zhou, et al. Enhanced NFjB and AP-1 transcriptional activity associated with antiestrogen resistant breast cancer. BMC Cancer. Apr. 3, 2007;7:59.
Malliri, et al., The transcription factor AP-1 is required for EGF-induced activation of rho-like GTPases, cytoskeletal rearrangements, motility, and in vitro invasion of A431 cells. J Cell Biol. Nov. 16, 1998;143(4):1087-99.
Stetler-Stevenson, Type IV collagenases in tumor invasion and metastasis. Cancer Metastasis Rev. Dec. 1990;9(4):289-303.
McMillan, et al., Pharmacological inhibition of gelatinase B induction and tumor cell invasion. Int J Cancer. Aug. 7, 1996;67(4):523-31.
Kawata, et al., Enhanced production of matrix metalloproteinase-2 in human head and neck carcinomas is correlated with lymph node metastasis. Acta Otolaryngol. Jan. 2002;122(1):101-6.
Hong, et al., Expression of matrix metalloproteinase-2 and -9 in oral squamous cell carcinomas with regard to the metastatic potential. Oral Oncol. Mar. 2000;36(2):207-13.
Rosenthal, et al., Matrix metalloproteases in head and neck cancer. Head Neck. Jul. 2006;28(7):639-648.
Westermarck, et al., Regulation of matrix metalloproteinase expression in tumor invasion. FASEB J. May 1999;13(8):781-92.
Spence, et al., AP-1 differentially expressed proteins Krp1 and fibronectin cooperatively enhance Rho-ROCK-independent mesenchymal invasion by altering the function, localization, and activity of non differentially expressed proteins. Mol Cell Biol. Feb. 2006;26(4):1480-95.
Kustikova, et al., Fra-1 induces morphological transformation and increases in vitro invasiveness and motility of epithelioid adenocarcinoma cells. Mol Cell Biol. Dec. 1998;18(12):7095-7105.
Belguise, et al., FRA-1 expression level regulates proliferation and invasiveness of breast cancer cells. Oncogene. Feb. 17, 2005;24(8):1434-44.
Wolff, et al., Expression of cyclooxygenase-2 in human lung carcinoma. Cancer Res. Nov. 15, 1998;58(22):4997-5001.
Marconcini, et al., c-fos-induced growth factor/vascular endothelial growth factor D induces angiogenesis in vivo and in vitro. Proc Natl Acad Sci U S A. Aug. 17, 1999;96(17):9671-9676.
Mazar, et al., The urokinase plasminogen activator system in cancer: implications for tumor angiogenesis and metastasis. Angiogenesis. 1999;3(1):15-32.
Wang, et al., Current and potential inflammation targeted therapies in head and neck cancer. Curr Opin Pharmacol. Aug. 2009;9(4):389-395.

Reichmann, et al., Activation of an inducible c-FosER fusion protein causes loss of epithelial polarity and triggers epithelial-fibroblastoid cell conversion. Cell. Dec. 24, 1992;71(7):1103-16.
Nguyen, et al., The FGFR1 inhibitor PD173074 induces mesenchymal-epithelial transition through the transcription factor AP-1. Br J Cancer. Oct. 15, 2013;109(8):2248-58.
Coussens, et al., Matrix metalloproteinase inhibitors and cancer—trials and tribulations. Science. Mar. 29, 2002;295(5564):2387-92.
Andreasen, et al., The urokinase-type plasminogen activator system in cancer metastasis: a review. Int J Cancer. Jul. 3, 1997;72(1):1-22.
Muraoka, et al., Blockade of TGF-b inhibits mammary tumor cell viability, migration, and metastases. J Clin Invest. Jun. 2002;109(12):1551-9.
Drevs, et al., Effects of PTK787/ZK 222584, a specific inhibitor of vascular endothelial growth factor receptor tyrosine kinases, on primary tumor, metastasis, vessel density, and blood flow in a murine renal cell carcinoma model. Cancer Res. Sep. 1, 2000;60(17):4819-24.
Sakai, et al., Most human squamous cell carcinomas in the oral cavity contain mutated p53 tumor-suppressor genes. Oncogene. May 1992;7(5):927-33.
Ichwan, et al., Defect in serine 46 phosphorylation of p53 contributes to acquisition of p53 resistance in oral squamous cell carcinoma cells. Oncogene. Feb. 23, 2006;25(8):1216-24.
Sano, et al., Disruptive TP53 mutation is associated with aggressive disease characteristics in an orthotopic murine model of oral tongue cancer. Clin Cancer Res. Nov. 1, 2011;17(21):6658-70.
Ye, et al., Small molecule inhibitors targeting activator protein 1 (AP-1). J Med Chem. Aug. 28, 2014;57(16):6930-48.
Avouac, et al., Inhibition of activator protein 1 signaling abrogates transforming growth factor b-mediated activation of fibroblasts and prevents experimental fibrosis. Arthritis Rheum. May 2012;64(5):1642-52.
Izuta, et al., T-5224, a selective inhibitor of c-Fos/activator protein-1, attenuates lipopolysaccharide-induced liver injury in mice. Biotechnol Lett. Dec. 2012;34(12):2175-82.
Miyazaki, et al., The effects of a selective inhibitor of c-Fos/activator protein-1 on endotoxininduced acute kidney injury in mice. BMC Nephrol. 2012;13:153.
Yoshida, et al., The impact of c-Fos/activator protein-1 inhibition on allogeneic pancreatic islet transplantation. Am J Transplant. Oct. 2015;15(10):2565-75.
Kamide, et al., Selective activator protein-1 inhibitor T-5224 prevents lymph node metastasis in an oral cancer model. Cancer Sci. May 2016;107(5):666-73.
Moon, et al., Effects of Coexistent BRAFV600E and TERT Promoter Mutations on Poor Clinical Outcomes in Papillary Thyroid Cancer: A Meta-Analysis. Thyroid. May 2017;27(5):651-660.
Liu, et al., Regulation of mutant TERT by BRAF V600E/MAP kinase pathway through FOS/GABP in human cancer. Nature Communications. Feb. 2018;9:579.
Santarpia, et al., Targeting the MAPK-RAS-RAF signaling pathway in cancer therapy. Expert Opin Ther Targets. Jan. 2012;16(1):103-19.
Burotto, et al., The MAPK pathway across different malignancies: a new perspective. Cancer. Nov. 15, 2014;120(22):3446-56.

\* cited by examiner

SEQ ID NO:33

SEQ ID NO:34

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: TERT-F

<400> SEQUENCE: 1
gtccgaggtg tccctgagta                                         20

<210> SEQ ID NO 2
<211> LENGTH: 20
<212> TYPE: DNA
<213> ORGANISM: Artificial Sequence
<220> FEATURE:
<223> OTHER INFORMATION: TERT-R

<400> SEQUENCE: 2
cagggcctcg tcttctacag                                         20

<210> SEQ ID NO 3
<211> LENGTH: 20
<212> TYPE: DNA
<213> ORGANISM: Artificial Sequence
<220> FEATURE:
<223> OTHER INFORMATION: GAPDH-F

<400> SEQUENCE: 3
tgcaccacca actgcttagc                                         20

<210> SEQ ID NO 4
<211> LENGTH: 21
<212> TYPE: DNA
<213> ORGANISM: Artificial Sequence
<220> FEATURE:
<223> OTHER INFORMATION: GAPDH-R

<400> SEQUENCE: 4
```
ggcatggact gtggtcatga g                                           21

<210> SEQ ID NO 5
<211> LENGTH: 28
<212> TYPE: DNA
<213> ORGANISM: Artificial Sequence
<220> FEATURE:
<223> OTHER INFORMATION: GABPA-F

<400> SEQUENCE: 5
ggggtaccac tgaccggcca aaggttag                                    28

<210> SEQ ID NO 6
<211> LENGTH: 28
<212> TYPE: DNA
<213> ORGANISM: Artificial Sequence
<220> FEATURE:
<223> OTHER INFORMATION: GABPA-R

<400> SEQUENCE: 6
ccctcgagtc ggaggggagc ttgaacta                                    28

<210> SEQ ID NO 7
<211> LENGTH: 28
<212> TYPE: DNA
<213> ORGANISM: Artificial Sequence
<220> FEATURE:
<223> OTHER INFORMATION: GABPB-F

<400> SEQUENCE: 7
ggggtacctc cttccgtctc ccaggatt                                    28

<210> SEQ ID NO 8
<211> LENGTH: 28
<212> TYPE: DNA
<213> ORGANISM: Artificial Sequence
<220> FEATURE:
<223> OTHER INFORMATION: GABPB-R

<400> SEQUENCE: 8
ccctcgagaa tccccaccga aaagtccc                                    28

<210> SEQ ID NO 9
<211> LENGTH: 26
<212> TYPE: DNA
<213> ORGANISM: Artificial Sequence
<220> FEATURE:
<223> OTHER INFORMATION: TERT-F

<400> SEQUENCE: 9
cgacgcgtgg ctcccagtgg attcgc                                      26

<210> SEQ ID NO 10
<211> LENGTH: 26
<212> TYPE: DNA
<213> ORGANISM: Artificial Sequence
<220> FEATURE:
<223> OTHER INFORMATION: TERT-R

<400> SEQUENCE: 10
ccgctcgagc ctcgcggtag tggctg                                      26

<210> SEQ ID NO 11
<211> LENGTH: 25
<212> TYPE: DNA
<213> ORGANISM: Artificial Sequence

```
<220> FEATURE:
<223> OTHER INFORMATION: FOS-T232A-F

<400> SEQUENCE: 11
ccagaggttg ccgccccgga gtctg                                    25

<210> SEQ ID NO 12
<211> LENGTH: 25
<212> TYPE: DNA
<213> ORGANISM: Artificial Sequence
<220> FEATURE:
<223> OTHER INFORMATION: FOS-T232A-R

<400> SEQUENCE: 12
cagactccgg ggcggcaacc tctgg                                    25

<210> SEQ ID NO 13
<211> LENGTH: 25
<212> TYPE: DNA
<213> ORGANISM: Artificial Sequence
<220> FEATURE:
<223> OTHER INFORMATION: FOS-T325A-F

<400> SEQUENCE: 13
gagcccctgt gcgctccggt ggtca                                    25

<210> SEQ ID NO 14
<211> LENGTH: 25
<212> TYPE: DNA
<213> ORGANISM: Artificial Sequence
<220> FEATURE:
<223> OTHER INFORMATION: FOS-T325A-R

<400> SEQUENCE: 14
tgaccaccgg agcgcacagg ggctc                                    25

<210> SEQ ID NO 15
<211> LENGTH: 27
<212> TYPE: DNA
<213> ORGANISM: Artificial Sequence
<220> FEATURE:
<223> OTHER INFORMATION: FOS-T331A-F

<400> SEQUENCE: 15
ggtggtcacc tgtgctccca gctgcac                                  27

<210> SEQ ID NO 16
<211> LENGTH: 27
<212> TYPE: DNA
<213> ORGANISM: Artificial Sequence
<220> FEATURE:
<223> OTHER INFORMATION: FOS-T331A-R

<400> SEQUENCE: 16
gtgcagctgg gagcacaggt gaccacc                                  27

<210> SEQ ID NO 17
<211> LENGTH: 25
<212> TYPE: DNA
<213> ORGANISM: Artificial Sequence
<220> FEATURE:
<223> OTHER INFORMATION: FOS-S374A-F

<400> SEQUENCE: 17
gactcgctca gcgcacccac gctgc                                    25
```

<210> SEQ ID NO 18
<211> LENGTH: 25
<212> TYPE: DNA
<213> ORGANISM: Artificial Sequence
<220> FEATURE:
<223> OTHER INFORMATION: FOS-S374A-R

<400> SEQUENCE: 18
gcagcgtggg tgcgctgagc gagtc                                           25

<210> SEQ ID NO 19
<211> LENGTH: 37
<212> TYPE: DNA
<213> ORGANISM: Artificial Sequence
<220> FEATURE:
<223> OTHER INFORMATION: BRAF-A1799T-F

<400> SEQUENCE: 19
attttggtct agctacagtg aaatctcgat ggagtgg                              37

<210> SEQ ID NO 20
<211> LENGTH: 37
<212> TYPE: DNA
<213> ORGANISM: Artificial Sequence
<220> FEATURE:
<223> OTHER INFORMATION: BRAF-A1799T-R

<400> SEQUENCE: 20
ccactccatc gagatttcac tgtagctaga ccaaaat                              37

<210> SEQ ID NO 21
<211> LENGTH: 23
<212> TYPE: DNA
<213> ORGANISM: Artificial Sequence
<220> FEATURE:
<223> OTHER INFORMATION: TERT-C228T-F

<400> SEQUENCE: 21
ggcccagccc cttccgggcc ctc                                             23

<210> SEQ ID NO 22
<211> LENGTH: 23
<212> TYPE: DNA
<213> ORGANISM: Artificial Sequence
<220> FEATURE:
<223> OTHER INFORMATION: TERT-C228T-R

<400> SEQUENCE: 22
gagggcccgg aaggggctgg gcc                                             23

<210> SEQ ID NO 23
<211> LENGTH: 23
<212> TYPE: DNA
<213> ORGANISM: Artificial Sequence
<220> FEATURE:
<223> OTHER INFORMATION: TERT-250T-F

<400> SEQUENCE: 23
ccgtcccgac ccttccggg tcc                                              23

<210> SEQ ID NO 24
<211> LENGTH: 23
<212> TYPE: DNA
<213> ORGANISM: Artificial Sequence
<220> FEATURE:
<223> OTHER INFORMATION: TERT-C250T-R

<400> SEQUENCE: 24
ggacccggaa ggggtcggga cgg                                              23

<210> SEQ ID NO 25
<211> LENGTH: 29
<212> TYPE: DNA
<213> ORGANISM: Artificial Sequence
<220> FEATURE:
<223> OTHER INFORMATION: GABPB-FOS-binding-mut-F

<400> SEQUENCE: 25
ggatgctggg agctagactc actcgcaca                                        29

<210> SEQ ID NO 26
<211> LENGTH: 29
<212> TYPE: DNA
<213> ORGANISM: Artificial Sequence
<220> FEATURE:
<223> OTHER INFORMATION: GABPB-FOS-binding-mut-R

<400> SEQUENCE: 26
tgtgcgagtg agtctagctc ccagcatcc                                        29

<210> SEQ ID NO 27
<211> LENGTH: 27
<212> TYPE: DNA
<213> ORGANISM: Artificial Sequence
<220> FEATURE:
<223> OTHER INFORMATION: GABPB-MUC-binding-mut-F

<400> SEQUENCE: 27
ctcactcgca cacgatgtgt ccctccg                                          27

<210> SEQ ID NO 28
<211> LENGTH: 27
<212> TYPE: DNA
<213> ORGANISM: Artificial Sequence
<220> FEATURE:
<223> OTHER INFORMATION: GABPB-MYC-binding-mut-R

<400> SEQUENCE: 28
cggagggaca catcgtgtgc gagtgag                                          27

<210> SEQ ID NO 29
<211> LENGTH: 18
<212> TYPE: DNA
<213> ORGANISM: Artificial Sequence
<220> FEATURE:
<223> OTHER INFORMATION: TERT-F

<400> SEQUENCE: 29
ggattcgcgg gcacagac                                                    18

<210> SEQ ID NO 30
<211> LENGTH: 17
<212> TYPE: DNA
<213> ORGANISM: Artificial Sequence
<220> FEATURE:
<223> OTHER INFORMATION: TERT-R

<400> SEQUENCE: 30
gggagcgcgc ggcatcg                                                     17

<210> SEQ ID NO 31

<211> LENGTH: 20
<212> TYPE: DNA
<213> ORGANISM: Artificial Sequence
<220> FEATURE:
<223> OTHER INFORMATION: GABPB-F

<400> SEQUENCE: 31
aaagattccg cactctccgt                                                    20

<210> SEQ ID NO 32
<211> LENGTH: 20
<212> TYPE: DNA
<213> ORGANISM: Artificial Sequence
<220> FEATURE:
<223> OTHER INFORMATION: GABPB-R

<400> SEQUENCE: 32
aatccccacc gaaaagtccc                                                    20

<210> SEQ ID NO 33
<211> LENGTH: 11
<212> TYPE: DNA
<213> ORGANISM: Homo sapiens

<400> SEQUENCE: 33
tacagtgaaa t                                                             11

<210> SEQ ID NO 34
<211> LENGTH: 11
<212> TYPE: DNA
<213> ORGANISM: Homo sapiens

<400> SEQUENCE: 34
tacagagaaa t                                                             11

<210> SEQ ID NO 35
<211> LENGTH: 26
<212> TYPE: DNA
<213> ORGANISM: Homo sapiens

<400> SEQUENCE: 35
cttgactcac tcgcacacca tgtgtc                                             26

<210> SEQ ID NO 36
<211> LENGTH: 380
<212> TYPE: PRT
<213> ORGANISM: Homo sapiens
<220> FEATURE:
<221> NAME/KEY: MISC_FEATURE
<222> LOCATION: (1)..(380)
<223> OTHER INFORMATION: Human c-Fos amino acid sequence (Uniprot
      P01100-1)

<400> SEQUENCE: 36

Met Met Phe Ser Gly Phe Asn Ala Asp Tyr Glu Ala Ser Ser Ser Arg
1               5                   10                  15

Cys Ser Ser Ala Ser Pro Ala Gly Asp Ser Leu Ser Tyr Tyr His Ser
            20                  25                  30

Pro Ala Asp Ser Phe Ser Ser Met Gly Ser Pro Val Asn Ala Gln Asp
        35                  40                  45

Phe Cys Thr Asp Leu Ala Val Ser Ser Ala Asn Phe Ile Pro Thr Val
    50                  55                  60

Thr Ala Ile Ser Thr Ser Pro Asp Leu Gln Trp Leu Val Gln Pro Ala
65                  70                  75                  80

```
                                          -continued

Leu Val Ser Ser Val Ala Pro Ser Gln Thr Arg Ala Pro His Pro Phe
             85                  90                  95

Gly Val Pro Ala Pro Ser Ala Gly Ala Tyr Ser Arg Ala Gly Val Val
            100                 105                 110

Lys Thr Met Thr Gly Gly Arg Ala Gln Ser Ile Gly Arg Arg Gly Lys
            115                 120                 125

Val Glu Gln Leu Ser Pro Glu Glu Glu Lys Arg Arg Ile Arg Arg
130                 135                 140

Glu Arg Asn Lys Met Ala Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
                165                 170                 175

Ser Ala Leu Gln Thr Glu Ile Ala Asn Leu Leu Lys Glu Lys Glu Lys
                180                 185                 190

Leu Glu Phe Ile Leu Ala Ala His Arg Pro Ala Cys Lys Ile Pro Asp
            195                 200                 205

Asp Leu Gly Phe Pro Glu Glu Met Ser Val Ala Ser Leu Asp Leu Thr
            210                 215                 220

Gly Gly Leu Pro Glu Val Ala Thr Pro Glu Ser Glu Glu Ala Phe Thr
225                 230                 235                 240

Leu Pro Leu Leu Asn Asp Pro Glu Pro Lys Pro Ser Val Glu Pro Val
                245                 250                 255

Lys Ser Ile Ser Ser Met Glu Leu Lys Thr Glu Pro Phe Asp Asp Phe
                260                 265                 270

Leu Phe Pro Ala Ser Ser Arg Pro Ser Gly Ser Glu Thr Ala Arg Ser
            275                 280                 285

Val Pro Asp Met Asp Leu Ser Gly Ser Phe Tyr Ala Ala Asp Trp Glu
            290                 295                 300

Pro Leu His Ser Gly Ser Leu Gly Met Gly Pro Met Ala Thr Glu Leu
305                 310                 315                 320

Glu Pro Leu Cys Thr Pro Val Val Thr Cys Thr Pro Ser Cys Thr Ala
                325                 330                 335

Tyr Thr Ser Ser Phe Val Phe Thr Tyr Pro Glu Ala Asp Ser Phe Pro
                340                 345                 350

Ser Cys Ala Ala Ala His Arg Lys Gly Ser Ser Ser Asn Glu Pro Ser
            355                 360                 365

Ser Asp Ser Leu Ser Ser Pro Thr Leu Leu Ala Leu
370                 375                 380
```

REGULATION OF MUTANT TERT BY BRAF V600E/MAP KINASE PATHWAY THROUGH FOS/GABP IN HUMAN CANCER

CROSS-REFERENCE TO RELATED APPLICATIONS

This application is a 35 U.S.C. § 371 U.S. national entry of International Application PCT/US2018/067419, having an international filing date of Dec. 22, 2018, which claims the benefit of U.S. Provisional Application No. 62/609,587, filed Dec. 22, 2017, the content of each of the aforementioned applications is herein incorporated by reference in their entirety.

STATEMENT OF GOVERNMENTAL INTEREST

This invention was made with government support under CA113507 and CA189224 awarded by the National Institutes of Health. The government has certain rights in the invention.

FIELD OF THE INVENTION

The present invention relates to the field of cancer. More specifically, the present invention provides methods and compositions useful for the treatment of cancer characterized by TERT and BRAF mutations.

INCORPORATION-BY-REFERENCE OF MATERIAL SUBMITTED ELECTRONICALLY

This application contains a sequence listing. It has been submitted electronically via EFS-Web as an ASCII text file entitled "P15106-02_ST25.txt." The sequence listing is 10,024 bytes in size, and was created on Dec. 20, 2018. It is hereby incorporated by reference in its entirety.

BACKGROUND OF THE INVENTION

Telomerase reverse transcriptase (TERT) is the catalytic component of the telomerase complex, which plays a key role in maintaining the telomere length of chromosomes and cell immortality and in controlling cellular activities.[1] Mutations in the TERT promoter were found initially in melanoma[2,3] and subsequently widely in other human cancers[11], including thyroid cancer.[5,6] Two recurrent TERT promoter mutations located at hotspots chr5, 1,295,228 C>T (C228T) and 1,295,250 C>T (C250T) are particularly common, which correspond to the positions 124 and 146 bp, respectively, upstream of the translation start site of TERT; both mutations are predicted to generate a consensus binding site for E-twenty-six (ETS) transcription factors[2,3]. Further studies showed that TERT promoter mutations were associated with higher levels of TERT expression, telomerase activities, and oncogenic cellular activities.[7,8,9,10]

BRAF V600E is another major human oncogene that was also initially discovered in melanoma and subsequently widely found in other human cancers[11], including thyroid cancer, particularly papillary thyroid cancer (PTC).[12] This mutation causes constitutive activation of the BRAF kinase and consequent oncogenic activation of the mitogen-activated protein kinase (MAPK) pathway through phosphorylating MEK and ERK. It has been widely observed that BRAF V600E is associated with aggressiveness of human cancer, as exemplified by increased tumor recurrence and disease-specific mortality of PTC[13,14] as well as clinico-pathological aggressiveness of melanoma[15,16] and other cancers such as colorectal cancer, and brain tumor.[15,17,18] TERT promoter mutations were similarly associated with increased aggressiveness of human cancers, as exemplified by increased tumor recurrence and disease-specific mortality of PTC[5] and aggressiveness of melanoma[9,19], glioma, and bladder cancer.[20,21] Interestingly, BRAF V600E was widely found to be associated with TERT promoter mutations in human cancers, particularly thyroid cancer and melanoma.[2,5,6,9,19,22,23] When separated from each other, either mutation alone had only a modest effect while coexisting BRAF V600E and TERT promoter mutations were associated with robustly increased cancer aggressiveness, as exemplified by increased lymph node metastasis, distant metastasis, advanced tumor stage, tumor recurrence, and disease-specific mortality of PTC.[24,25,26,27] In a recent large meta analysis on PTC[5], the prevalence of coexistence of BRAF V600E and TERT promoter mutations was 7.7% (145/1892), which impressively numerically corresponds to the conventionally known <10% of patients with PTC that has the poorest clinical outcomes. In melanoma, coexistence of BRAF V600E and TERT promoter mutations was associated with increased tumor thickness, high mitotic rate, lymph node metastasis, presence of ulceration, absence of regression, high risk of tumor recurrence, and melanoma-specific mortality.[22,23]

These results establish that the unique oncogene duet of coexisting BRAF V600E and TERT promoter mutations is a fundamental genetic background that cooperatively drives progression and aggressiveness of some human cancers. However, the molecular mechanism underpinning the synergistic oncogenic operations of the two oncogenes is undefined. Specifically, a fundamental question as to how BRAF V600E and mutant TERT, which each apparently represents a different molecular system, are functionally bridged at the molecular level in cooperatively promoting human cancer aggressiveness remains to be answered.

SUMMARY OF THE INVENTION

The present inventors mechanistically explored this issue by testing the hypothesis that the BRAF V600E-activated MAPK pathway may selectively upregulate the mutant TERT through a molecular mechanism that mediates the activation of the mutant TERT promoter-selective transcriptional machinery, thus functionally connecting the two oncogenes in cooperatively promoting oncogenesis. The present invention is based, at least in part, on the identification of FOS as playing such a critical role in this important mechanism of human oncogenesis. Specifically, the present inventors identified a molecular mechanism for the activation of mutant TERT by the BRAF V600E/MAP kinase pathway, in which FOS as a transcriptional factor of the GABPB promoter promotes the expression of GABPB; the latter complexes with GABPA and selectively binds and activates the mutant TERT promoter, robustly upregulating the expression of TERT, thus functionally bridging the two oncogenes in cooperatively promoting oncogenesis.

As described herein, the present inventors demonstrated that a FOS inhibitor can inhibit preferentially cancer cells that harbor TERT promoter mutations, providing a novel strategy of targeting FOS in the recently discovered novel BRAF/MAPK/FOS/GABP/TERT pathway in a TERT mutation-guided manner for the treatment of human cancer.

Accordingly, in one aspect, the present invention provides methods of treatment of a mutant telomerase reverse transcriptase (TERT) enzyme-associated cancer. In particular embodiments, the method comprises the step of administering to the subject an anti-cancer agent that inhibits FOS. In further embodiments, an agent is administered that inhibits GABPB, the formation of the GABPA-GABPB complex or the binding of the GABPA-GABPB complex to a mutant TERT promoter.

In a specific embodiment, a method for treating a mutant telomerase reverse trancriptase (TERT) enzyme-associated cancer in a subject comprises the step of administering to the subject a FOS inhibitor. In certain embodiments, the mutant TERT enzyme-associated cancer comprises a C228T and/or C250T mutation. In another embodiment, the subject has a mutation in the BRAF gene. In a more specific embodiment, the BRAF mutation is BRAF V600E.

The FOS inhibitor can comprise a benzophenone derivative. In a specific embodiment, the benzophenone derivative comprises 3-{5-[4-(cyclopentyloxy)-2-hydroxybenzoyl]-2-[(3-hydroxyl-1,2-benzisoxazo-1-6-yl)methoxy]phenyl}propanoic acid (T-5224). In other embodiments the benzophenone derivative is selected from the group consisting of: 3-{5-[4-(cyclopentyloxy)-2-hydroxybenzoyl]-2-[(3-hydroxyl-1,2-benzisoxazo-1-6-yl)methoxy}phenyl}propanoic acid; 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate; 4-({2-(2-carboxyethyl)-4-[4-(cyclopentyloxy)-2-hydroxybenzoyl]phenoxy}methyl)benzoic acid; and 3-(5-[4-(cyclopentyloxy)-2-hydroxybenzoyl]-2-{[4-(3-hydroxy-5-isoxazolyl)-benzyl]oxy}phenyl)propanoic acid.

The FOS inhibitor can comprise a derivative of retinoic acid. In a specific embodiment, the derivative of retinoic acid comprises (2E,4E,6Z,8E)-3-methyl-7-(4-methylphenyl)-9-(2,6,6-trimethylcyclohexen-1-yl)-2,4,6,8-nonatetraenoic acid (SR11302). In other embodiments, the derivative of retinoic acid is selected from the group consisting of: (2E,4E,6Z,8E)-3-methyl-7-(4-methylphenyl)-9-(2,6,6-trimethylcyclohexen-1-yl)-2,4,6,8-nonatetraenoic acid (SR11302); (2-(3,4-dihydro-4,4-dimethyl-2H-1-benzopyran-6-yl)-2-(4-carboxyphenyl)-1,3-dithiane (SR11238); (E)-4-(2-(5,6,7,8-tetrahydro-5,5,8,8-tetramethyl-2-naphthalenyl)-3-phenylpropenyl)benzoic acid (SR11327); methyl (Z)-4-(1-acetoxy-2-(5,6,7,8-tetrahydro-5,5,8,8-tetramethyl-2-naphthalenyl)ethenyl)benzoate (SR11220) and 5-((5,6,7,8-tetrahydro-5,5,8,8-tetramethyl-2-naphthalenyl)carbonyl)-2-naphthalenecarboxylic acid (SR11228).

In further embodiments, the FOS inhibitor comprises curcumin, difluorinated curcumin (DFC) or dihydroguaiaretic acid (DHGA).

In another specific embodiment, the method further comprises administering a TERT inhibitor. In a more specific embodiment, the TERT inhibitor comprises 2-[(E)-3-naphthen-2-yl but-2-enoylamino]benzoic acid (BIBR1532) and derivatives thereof.

In certain embodiments, the method further comprises administering a BRAF inhibitor. In a specific embodiment, the BRAF inhibitor is selected from the group consisting of vemurafenib, dabrafenib, encorafenib and derivatives of the foregoing.

In another embodiment, the method further comprise administering a MEK inhibitor. In a specific embodiment, the MEK inhibitor is selected from the group consisting of cobimetinib, binimetinib, trametinib and derivatives of the foregoing.

In certain embodiments, the present invention provides a FOS inhibitor for use in the treatment of a mutant TERT enzyme-associated cancer in a subject. In other embodiments, the present invention provides the use of a FOS inhibitor in the manufacture of a medicament for the treatment of a mutant TERT enzyme-associated cancer in a subject.

The administration of the foregoing embodiments include the administration in an effective amount to treat the mutant TERT-associated cancer. The present invention also contemplates compositions comprising combinations of the foregoing, i.e., a FOS inhibitor, a TERT inhibitor, a BRAF inhibitor and/or a MEK inhibitor.

BRIEF DESCRIPTION OF THE FIGURES

In FIG. 1A, the P values are for the comparison of the indicated condition with "BRAF/TERT knockdown (KD)" (red line). In FIG. 1F, the P values are for the comparison of the indicated condition with "PLX4032/shTERT" (red line).

(FIG. 2A) TERT expression was analyzed by qRT-PCR in cells treated with 0.5 uM PLX4032 or 0.2 uM AZD6244 for 24 hours (upper panel). The corresponding levels of phosphorylated ERK (p-ERK), total ERK (t-ERK), and beta-actin were detected by Western blotting (lower panel). The relative TERT mRNA expression levels were normalized to the DMSO control group. (FIG. 2B) Luciferase reporting assay of TERT promoter activities in K1 cells treated with DMSO or PLX4032 (0.5 uM). (FIG. 2C, 2D) Specific shRNA against BRAF were used to knock down BRAF in thyroid cancer cell lines BCPAP and K1 and melanoma cell line A375. Scramble shRNA was used as control. Cells were then subjected to Western blotting (FIG. 2C) and qRT-PCR (FIG. 2D). (FIG. 2E) Sequencing of the BRAF exon-15 in the parental and heterozygous BRAF-V600E knock-in SW48 cells. BRAF V600E was knocked in on one allele of BRAF by rAAV technology through homologous recombination and Cre recombinase of the Neo cassette. (FIG. 2F) Western blotting analyses of phosphorylation of ERK (p-ERK), total ERK (t-ERK), BRAF, and beta-actin in the parental and BRAF-V600E knock-in SW48 cells. (FIG. 2G) TERT promoter luciferase reporter assay in SW48 cells with/without BRAF V600E knock-in. P<0.01, *P<0.001, by 2-tailed Student's t test. P values are for the comparison of the indicated condition with DMSO (FIG. 2B), scramble (FIG. 2D), or BRAF-WT groups (FIG. 2G). All the values represent the average standard deviation (SD) of triplicate samples from a typical experiment. All the experiments were performed three times with similar results.

(FIG. 3A) The four indicated cancer cell lines harboring BRAF V600E mutation were treated with 0.5 uM PLX4032 and/or 10 nM MYC-specific siRNA (siMYC) for 24 hours, which were then subjected to Western blotting (upper panel) and qRT-PCR (lower panel). The relative TERT mRNA expression was normalized to the control group. (FIG. 3B, 3C) Parental and BRAF V600E knock-in SW48 cells were treated with control siRNA (siControl) or MYC-specific siRNA (siMYC, 10 nM) for 48 h, followed by Western blotting (FIG. 3B) and luciferase reporter assays (FIG. 3C). *P<0.05, P<0.01, *P<0.001, by 2-tailed Student's t test. n.s., not significant. All the values represent the average standard deviation (SD) of triplicate samples from a typical experiment. Similar results were obtained in two additional independent experiments.

(FIG. 4A) Chromatin-immunoprecipitation (ChIP) assay for GABPA and GABPB occupancy at TERT promoter in K1 and A375 cells with TERT promoter mutation and in WRO and HTORI3 cells without promoter mutation. IgG was used as negative control. (FIG. 4B) Co-immunoprecipitation (Co-IP) analysis of the interaction of GABPA with GABPB in K1 cells. (FIG. 4C) ChIP assay for GABPA occupancy at TERT promoter in K1 and A375 cells with or without stable BRAF knockdown. (FIG. 4D) Western blotting analyses of GABPA, GABPB, and beta-actin in K1 and A375 cells with/without stable BRAF knockdown. (FIG. 4E) Luciferase reporter assays for GABPA and GABPB promoters in A375 cells with or without stable BRAF knockdown. Scramble shRNA was used as control. *P<0.05, ***P<0.001, by 2-tailed Student's t test. n.s., not significant. All the values represent the average standard deviation (SD) of triplicate samples and similar results were obtained in at least two independent experiments.

(FIG. 5A) Diagrammatic illustration of the putative FOS- and MYC-binding sites in the 5'-UTR of GABPB identified by bioinformatics analyses. The predicted palindromic FOS consensus binding site (5'-TGACTCA-3') and the canonical MYC binding site (5'-CATGTG-3') located at +222 to +228 and +238 to +243, downstream of the transcriptional start site, respectively. (FIG. 5B) GABPB 5'-UTR region-luciferase-reporter assays for the wild-type and artificially-induced mutated putative FOS- and MYC-binding sites. (FIG. 5C) ChIP assay for FOS and MYC occupancy at the 5'-UTR of GABPB in K1 and A375 cells. Pol II and IgG were used for positive and negative controls, respectively. (FIG. 5D) Western blotting analyses of GABPB, MYC, FOS, and beta-actin in K1 cells with stable FOS or MYC knockdown. (FIG. 5E) TERT promoter-luciferase reporter assays in K1 cells with stable FOS knockdown. (FIG. 5F) Western blotting analyses for TERT, FOS, and beta-actin in K1, A375 and WRO cells with or without stable FOS knockdown. *P<0.05, **P<0.01, by 2-tailed Student's t test. n.s., not significant. All values represent the average±standard deviation (SD) of triplicate samples, and similar results were obtained in three independent experiments.

(FIG. 6A) Western blotting analyses for phosphorylated-FOS (p-FOS), total FOS (t-FOS), BRAF, and beta-actin in K1 and A375 cells with or without stable BRAF knockdown. (FIG. 6B) Western blotting analyses of p-FOS, t-FOS, p-ERK, and beta-actin in K1 and A375 cells treated with 0.5 uM PLX4032 for 0, 1, and 24 hours. (FIG. 6C-6E) Effects of FOS phosphorylation on GABPB and TERT activation. (FIG. 6C) KAT18 cells were serum-starved for 24 hours and transiently transfected with FOS wild-type (FOS-wt) or mutant (FOS-mut) bearing none of the potential ERK-targeted phosphorylation sites, followed by Western blotting analysis for TERT, GABPB, p-FOS, t-FOS, and beta-actin. (FIG. 6D) KAT18 cells were transfected with FOS-wt or FOS-mut along with GABPB 5'-UTR luciferase reporter and Renilla luciferase (pRL-TK) plasmids in the absence of serum for 24 hours, and the luciferase activities were then measured. (FIG. 6E) KAT18 cells were transiently transfected with FOS-wt or FOS-mut, together with TERT promoter luciferase reporters harboring the C228T or C250T mutation, and pRL-TK for 24 hours, followed by luciferase assays. (FIG. 6F) ChIP assay for FOS binding to the 5'-UTR of GABPB in K1 and A375 cells. (FIG. 6G) Western blotting analyses for GABPB, p-FOS, p-ERK, and t-ERK in the parental and BRAF-V600E knock-in SW48 cells. (FIG. 6H) ChIP assay for FOS binding to the 5'-UTR of GABPB in SW48 cells. (FIG. 6) GABPB 5'-UTR region-luciferase reporter assays in SW48 cells. (FIG. 6J) Wild-type (WT) BRAF and BRAF V600E were stably introduced to express in WRO cells, followed by Western blotting analyses of the expression of GABPB, p-FOS, BRAF, p-ERK, and t-ERK after serum starving overnight. P<0.01, *P<0.001, by 2-tailed Student's t test. n.s., not significant. All values represent the average standard deviation (SD) of triplicate samples and similar results were obtained in two additional independent experiments.

(FIG. 10A) Cell lines harboring TERT promoter mutation or wild-type TERT were seeded in 96-well plates and treated with T-5224 at increasing concentration for 5 days, followed by MTT assay. T-5224 with fresh cell culture medium containing 0.5% serum was replenished daily. Data represent relative cell viability at each indicated concentration of T-5224 in comparison with the vehicle (DMSO). (FIG. 10B) Comparison of the average inhibition rates of T-5224 between the group of TERT mutation-positive cells and the group of TERT mutation-negative cells at 10 µM and 20 µM T-5224. Data were presented as mean standard deviation. The P values were calculated by two-tailed Student's t-test.

DETAILED DESCRIPTION OF THE INVENTION

Figure 1A:
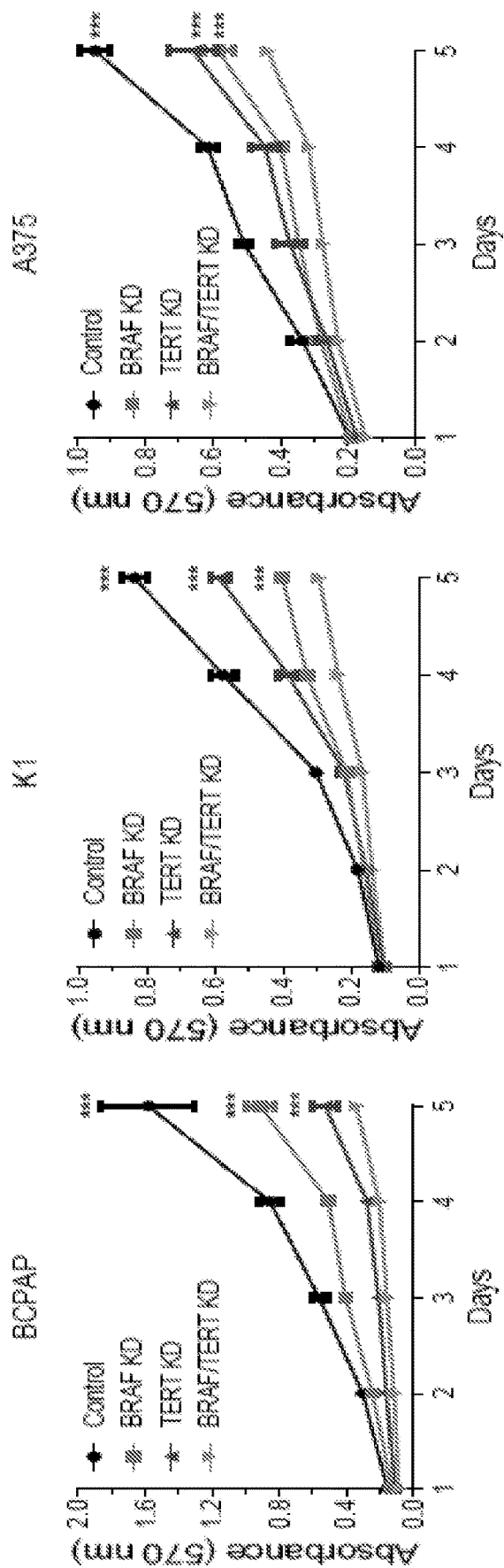
FIG. 1A-1G. Cooperative role of BRAF V600E and TERT in the oncogenic behavior and tumor growth of cancer cells. Specific shRNA against BRAF and siRNA against TERT were used to knock down BRAF and TERT in the indicated cancer cells, respectively, followed by performance of assays of MTT of cell proliferation (FIG. 1A), transwell cell migration (FIG. 1B), cell invasion (FIG. 1C), and colony formation in soft agar (FIG. 1D) (with representative images shown in the left panel and the average colony numbers in the right panel). Western blotting analysis of TERT and phosphorylation of ERK (p-ERK) was performed for K1 cells (FIG. 1E), from which xenograft tumors were derived to test the role of TERT and BRAF V600E in tumor development and growth (FIG. 1F, FIG. 1G). Panel f shows the time course of tumor growth and panel g shows the weights of tumors surgically excised. The "Control" in FIG. 1A-1D represented the combination of scramble shRNA and Control siRNA. The "Control" in FIG. 1E-G represented the combination of scramble shRNA and DMSO. The horizontal bar in FIGS. 1B and 1C represents 100 μm. The red horizontal bar on the left of FIG. 1D represents 100 μm; colonies larger than this size were counted and colony numbers are shown on the right of the panel. Little vertical bars in FIGS. 1A, 1D, 1F and 1G represent standard deviation (SD). *P<0.05, P<0.01, *P<0.001, by 2-tailed Student's t test.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The unique oncogene duet of coexisting BRAF V600E and TERT promoter mutations are widely found to be a robust genetic background promoting human cancer aggressiveness, but the mechanism is unclear. Here, we demonstrate that the BRAF V600E/MAP kinase pathway phosphorylates and activates FOS, which in turn acts as a transcription factor to bind and activate the GABPB promoter, increasing GABPB expression and driving formation of GABPA-GABPB complex; the latter selectively binds and activates mutant TERT promoter, upregulating TERT expression. Elevated TERT functions as a strong oncoprotein, robustly promoting aggressive behaviors of cancer cells and tumor development. We thus identify a molecular mechanism for the activation of mutant TERT by the BRAF V600E/MAP kinase pathway, in which FOS as a transcriptional factor of GABPB promoter plays a key role in functionally bridging the two oncogenes in cooperatively promoting oncogenesis, providing important cancer biological and clinical implications. These results particularly reveal FOS and GABPB as novel therapeutic targets using specific agents or drugs to treat thyroid cancer, melanoma and other human cancers that are positive for TERT promoter mutations.

These results described herein demonstrate, inter alia, that a FOS inhibitor can inhibit preferentially cancer cells that harbor TERT promoter mutations, providing a novel strategy of targeting FOS in the recently discovered novel BRAF/MAPK/FOS/GABP/TERT pathway in a TERT mutation-guided manner for the treatment of human cancer. The novelty of the implication of these results is two-fold: one, this for the first time demonstrates that FOS can be a specific target that is druggable in the novel BRAF/MAPK/FOS/GABP/TERT pathway; two, the therapeutic effect of targeting FOS in this pathway is TERT promoter mutation-dependent. Thus, clinically, effort can be made to identify patients with cancer that is TERT mutation-positive and then treat these patients with FOS inhibitor, such as T-5224. This will result in the best therapeutic effect with FOS inhibitors and constitutes a novel treatment strategy for human cancer.

Accordingly, in one aspect, the present invention provides compositions and methods for treating cancer. In particular embodiments, the present invention utilizes inhibitors of FOS. In a specific embodiment, a method for treating a mutant telomerase reverse trancriptase (TERT) enzyme-associated cancer in a subject comprises the step of administering to the subject an anti-cancer agent that inhibits one or more of FOS, GABPB, the formation of the GABPA-GABPB complex or the binding of the GABPA-GABPB complex to a mutant TERT promoter.

In particular embodiments, the Fos inhibitor can be an inhibitor of the Fos gene and/or the Fos protein.

In specific embodiments, inhibitors of Fos include, but are not limited to, curcumin, difluorinated curcumin (DFC); 3-(5-(4-(cyclopentyloxy)-2-hydroxybenzoyl)-2-((3-oxo-2,3-dihydrobenzo[d]isoxazol-6-yl)methoxy)phenyl)propanoic acid or salt thereof (T5224) (see U.S. Pat. No. 8,093,289); nordihydroguaiaretic acid (NDGA); dihydroguaiaretic acid (DHGA); and 3-[5-[4-(cyclopentyloxy)-2-hydroxybenzoyl]-2-[(3-hydroxy-1,2-benzisoxazol-6-yl)methoxy]phenyl]propionic acid or salt thereof (SR11302, Tocris Biosciences).

In further embodiments, the FOS inhibitor comprises gefitinib or erlotinib (Jimeno et al., 66(4) CANCER RES. 2385-90 (2006)).

In particular embodiments, the FOS inhibitor is a benzophenone derivative including, but not limited to, T-5224. See U.S. Pat. No. 7,772,285, which is fully incorporated herein by reference. Examples of other benzophenone derivatives include: 3-{5-[4-(cyclopentyloxy)-2-hydroxybenzoyl]-2-[(3-hydroxyl-1,2-benzisoxazo-1-6-yl) methoxy]phenyl}propanoic acid; 2-(4-morpholinyl)ethyl 3-{5-[4-(cyclopentyloxy)-2-hydroxybenzoyl]-2-[(3-hydroxy-1,2-benzisoxazol-6-yl)methoxy]phenyl}propanoate; 4-({2-(2-carboxyethyl)-4-[4-(cyclopentyloxy)-2-hydroxybenzoyl]phenoxy}methyl)benzoic acid; and 3-(5-[4-(cyclopentyloxy)-2-hydroxybenzoyl]-2-{[4-(3-hydroxy-5-isoxazolyl)-benzyl]oxy}phenyl)propanoic acid.

Further FOS inhibitors include, but are not limited to, dihydromyricetin (ampelopsin, (2R,3R)-3,5,7-trihydroxy-2-(3,4,5-trihydroxyphenyl)-2,3-dihydrochromen-4-one); 3,9-bis((ethylthio)methyl)-K-252a; anthra[1,9-cd]pyrazole-6-(2H)-one (SP600125, an anthrapyrazolone ATP-competitive inhibitor); anthraquinone derivatives; (R)-4-(4-methylpentanoyl)-8-(4-methylpentylidene)-1-thia-4-azaspiro[4.5]decane-3-carboxylic acid; (R)-8-(3-methylbutylidene)-4-(5-methylhexanoyl)-1-thia-4-azaspiro[4.5]decane-3-carboxylic acid; and 3-[2-isobutoxy-5-(4-isobutoxybenzoyl) phenyl)propionic acid (Tsuchida et al., 49 J. MED. CHEM. 80-91 (2006)

In other embodiments, the FOS inhibitor comprises a derivative of retinoic acid including, but not limited to, SR1302 ((2E,4E,6Z,8E)-3-methyl-7-(4-methylphenyl)-9-(2,6,6-tnmethylcyclohexen-1-yl)-2,4,6,8-nonatetraenoic acid);

SR11238 (2-(3,4-dihydro-4,4-dimethyl-2H-1-benzopyran-6-yl)-2-(4-carboxyphenyl)-1,3-dithiane); SR11327 ((E)-4-(2-(5,6,7,8-tetrahydro-5,5,8,8-tetramethyl-2-naphthalenyl)-3-phenylpropenyl)benzoic acid); SR11220 (methyl (Z)-4-(1-acetoxy-2-(5,6,7,8-tetrahydro-5,5,8,8-tetramethyl-2-naphthalenyl)ethenyl)benzoate) and SR11228 (5-((5,6,7,8-tetrahydro-5,5,8,8-tetramethyl-2-naphthalenyl)carbonyl)-2-naphthalenecarboxylic acid). See Fanjul et al., 372 NATURE 107-11(1994).

In certain embodiments, the method can further comprise administering a TERT inhibitor. In a specific embodiment, the TERT modulator is the antagonist BIBR1532 (2-[(E)-3-naphthen-2-yl but-2-enoylamino]benzoic acid). See Ward & Autexier, Mol. Pharmacol. 68:779-786, 2005; also J. Biol. Chem. 277(18):15566-72, 2002). TERT modulator antagonists can also include TMPyP4 (tetra-(N-methy-4-pyridyl) porphyrn); telomerase inhibitor IX (MST312), MnTMPyp pentachloride; BPPA; β-Rubromycin; Trichostatin A; Costunolide; Doxorubicin; Suramin Sodum; (–)-Epigallocatchin Gallate (and other catechins); triethylene tetraamine; geldanamycin; 17-(allylamino)-17-demethoxygeldanamycin. In another embodiment, a TERT inhibitor comprises azidothymidine (AZT).

In particular embodiments, the method can also comprise detecting a TERT mutation in the patient. In other embodiments, the method comprises detecting BRAF mutation in the patient.

In a further embodiment, the method can further comprise administering a BRAF inhibitor. Examples of BRAF inhibitors include Sorafenib (Bay 43-9006, Nexavar), Vemurafenib (PLX4032), BDC-0879, PLX-4720, Dabrafenib (Tafinlar), and Encorafenib (LGX818), RAF265 (CHIR-265) AZ628 and derivatives of the foregoing.

In yet another embodiment, the method can comprise administering a MEK inhibitor. Examples of MEK inhibitors include trametinib (GSK1120212), selumetinib (AZD6244), PD184352 (CI1040), PD0325901, RDEA119 (refametinib, BAY 869766), cobimetinib (GDC-0973, RF7420), binimetinib (MEK162, ARRY-162, ARRY-438162), Pimasertib (AS-703026), TAK-733, BI-847325, GDC-0623, PD98059, and derivatives of the foregoing.

The present invention thus contemplates combination therapy of any of the foregoing. For example, in one embodiment, a FOS inhibitor can be administered in conjunction with Binimetinib and Encorafenib. In another embodiment, a FOS inhibitor can be administered in conjunction with Cobimetinib and Vemurafenib.

Examples of mutant TERT associated cancer include, but are not limited to, melanoma, thyroid, bladder, glioblastoma, kidney. Further examples of cancer generally include carcinoma, lymphoma, blastoma, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, thyroid cancer, hepatic carcinoma, as well as head and neck cancer.

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Cell Lines.

We used the cell lines originally from the following providers to whom we are very grateful: Thyroid cancer cell line OCUT1 was originally from Dr. Naoyoshi Onoda (Osaka City University Graduate School of Medicine, Osaka, Japan); BCPAP was from Dr. Massimo Santoro (University of Federico II, Naples, Italy); K1 was from Dr. David Wynford-Thomas (University of Wales College of Medicine, Cardiff, United Kingdom); TPC1 cell line was from Dr. Alan P. Dackiw (Johns Hopkins University, Baltimore, Maryland); KAT18 was from Dr. Kenneth B. Ain (University of Kentucky Medical Center, Lexington, KY); C643 from Dr. N. E. Heldin (University of Uppsala, Uppsala, Sweden); WRO was from Dr. Guy J. F. Juillard (University of California-Los Angeles School of Medicine, Los Angeles, CA); FB1 was originally from Dr. Fulvio Basolo (UniversitA degli Studi di Pisa, Pisa, Italy). Normal thyroid epithelial cell line-derived HTORI-3 was originally from Dr. N. R. Lemoine (Hammersmith Hospital, London, UK). Melanoma cell lines A375, M14, SK-MEL-1, SK-MEL-2, SK-MEL-3, CHL-1 and MeWo, colon cancer cell line RKO, and human embryonic kidney 293T cells were purchased from American Type Culture Collection (ATCC). These cells were cultured in growth media as previously documented.[50, 51] The colon cell line SW48 with heterozygous knock-in of BRAF V600E mutation and the parental SW48 cells were purchased from Horizon Discovery (#HD 103-003, Cambridge, United Kingdom). The heterozygous knock-in of BRAF-activating mutation (V600E) was generated by rAAV technology through homologous recombination and Cre recombinase of the Neo cassette. One allele was knocked in with BRAF V600E. It was verified that there was no selection cassette at the engineered locus. The BRAF V600E knock-in and the parental SW48 cells were grown at 37° C. in RPMI-1640 medium with 10% fetal bovine serum (#F2442; Sigma-Aldrich, St Louis, MO). The status of TERT promoter and BRAF V600E mutations in these cells were analyzed as we described previously.[6, 52] The K1 cell line is reported to be contaminated with the GLAG-66 cell line in the International Cell Line Authentication Committee (ICLAC) database. These two cell lines are both human PTC-derived. Our genetic analysis of the K1 cell line used in the present study confirmed typical heterozygous BRAF V600E and TERT C228T mutations. Therefore, the K1 cell used here met the purpose of the present study to investigate the role of BRAF V600E and TERT promoter mutations in human cancer.

Inhibitors.

The BRAF V600E-specific inhibitor PLX4032 (#S1267) and the MEK1 inhibitor AZD6244 (#S1008) were purchased from Selleck Chemicals (Houston, TX), dissolved in DMSO with a stock concentration of 10 mM and stored at −20° C. PLX4032 and AZD6244 were used to treat cells for 24 hours at 0.5 μM and 0.2 μM, respectively, where indicated in the manuscript. DMSO was used as the vehicle control.

RNA Extraction and Quantitative Real-Time PCR (qRT-PCR).

Total RNA was extracted from cultured cells using the TRIzol reagent (#15596-018; Ambion, Life Technologies, Carlsbad, CA) and reverse-transcribed to cDNA using the SuperScript III First-Strand Synthesis System (#18080-051; Invitrogen, Life Technologies, Carlsbad, CA). Gene expression was analyzed in triplicate using FastStart Universal SYBR Green Master with ROX (#04913850001; Roche Applied Science, Indianapolis, IN) on the Applied Biosystems 7900HT Fast Real-Time PCR System. Relative expression of each gene was calculated according to the $2^{-\Delta\Delta Ct}$ method.[53] GAPDH was used as an internal control for normalization. Primers used for qRT-PCR were listed in Table 1.

TABLE 1

Primer sequences for RT-PCR, luciferase reporters cloning, mutagenesis and ChIP assays.

| Name | Primer Sequence 5'-3' |
| --- | --- |
| qRT-PCR | |
| TERT-F | 5'-GTCCGAGGTGTCCCTGAGTA-3' (SEQ ID NO: 1) |
| TERT-R | 5'-CAGGGCCTCGTCTTCTACAG-3' (SEQ ID NO: 2) |
| GAPDH-F | 5'-TGCACCACCAACTGCTTAGC-3' (SEQ ID NO: 3) |
| GAPDH-R | 5'-GGCATGGACTGTGGTCATGAG-3' (SEQ ID NO: 4) |
| Luciferase reporter constructs | |
| GABPA-F | 5'-GGGGTACCACTGACCGGCCAAAGGTTAG-3' (SEQ ID NO: 5) |
| GABPA-R | 5'-CCCTCGAGTCGGAGGGGAGCTTGAACTA-3' (SEQ ID NO: 6) |
| GABPB-F | 5'-GGGGTACCTCCTTCCGTCTCCCAGGATT-3' (SEQ ID NO: 7) |
| GABPB-R | 5'-CCCTCGAGAATCCCCACCGAAAAGTCCC-3' (SEQ ID NO: 8) |
| TERT-F | 5'-CGACGCGTGGCTCCCAGTGGATTCGC-3' (SEQ ID NO: 9) |
| TERT-R | 5'-CCGCTCGAGCCTCGCGGTAGTGGCTG-3' (SEQ ID NO: 10) |
| Mutagenesis | |
| FOS-T232A-F | 5'-CCAGAGGTTGCCGCCCCGGAGTCTG-3' (SEQ ID NO: 11) |
| FOS-T232A-R | 5'-CAGACTCCGGGGCGGCAACCTCTGG-3' (SEQ ID NO: 12) |
| FOS-T325A-F | 5'-GAGCCCCTGTGCGCTCCGGTGGTCA-3' (SEQ ID NO: 13) |

TABLE 1-continued

Primer sequences for RT-PCR, luciferase reporters cloning, mutagenesis and ChIP assays.

| Name | Primer Sequence 5'-3' |
| --- | --- |
| FOS-T325A-R | 5'-TGACCACCGGAGCGCACAGGGGCTC-3' (SEQ ID NO: 14) |
| FOS-T331A-F | 5'-GGTGGTCACCTGTGCTCCCAGCTGCAC-3' (SEQ ID NO: 15) |
| FOS-T331A-R | 5'-GTGCAGCTGGGAGCACAGGTGACCACC-3' (SEQ ID NO: 16) |
| FOS-S374A-F | 5'-GACTCGCTCAGCGCACCCACGCTGC-3' (SEQ ID NO: 17) |
| FOS-S374A-R | 5'-GCAGCGTGGGTGCGCTGAGCGAGTC-3' (SEQ ID NO: 18) |
| BRAF-A1799T-F | 5'-ATTTTGGTCTAGCTACAGTGAAATCTCGAT GGAGTGG-3' (SEQ ID NO: 19) |
| BRAF-A1799T-R | 5'-CCACTCCATCGAGATTTCACTGTAGCTAGA CCAAAAT-3' (SEQ ID NO: 20) |
| TERT-C228T-F | 5'-GGCCCAGCCCCTTCCGGGCCCTC-3' (SEQ ID NO: 21) |
| TERT-C228T-R | 5'-GAGGGCCCGGAAGGGGCTGGGCC-3' (SEQ ID NO: 22) |
| TERT-C250T-F | 5'-CCGTCCCGACCCCTTCCGGGTCC-3' (SEQ ID NO: 23) |
| TERT-C250T-R | 5'-GGACCCGGAAGGGGTCGGGACGG-3' (SEQ ID NO: 24) |
| GABPB-FOS-binding-mut-F | 5'-GGATGCTGGGAGCTAGACTCACTCGCACA-3' (SEQ ID NO: 25) |
| GABPB-FOS-binding-mut-R | 5'-TGTGCGAGTGAGTCTAGCTCCCAGCATCC-3' (SEQ ID NO: 26) |
| GABPB-MYC-binding-mut-F | 5'-CTCACTCGCACACGATGTGTCCCTCCG-3' (SEQ ID NO: 27) |
| GABPB-MYC-binding-mut-R | 5'-CGGAGGGACACATCGTGTGCGAGTGAG-3' (SEQ ID NO: 28) |
| CHiP assay | |
| TERT-F | 5'-GGATTCGCGGGCACAGAC-3' (SEQ ID NO: 29) |
| TERT-R | 5'-GGGAGCGCGCGGCATCG-3' (SEQ ID NO: 30) |
| GABPB-F | 5'-AAAGATTCCGCACTCTCCGT-3' (SEQ ID NO: 31) |
| GABPB-R | 5'-AATCCCCACCGAAAAGTCCC-3' (SEQ ID NO: 32) |

Western Blotting.

Cells were lysed in the RIPA buffer (#sc-24948; Santa Cruz Biotechnology, Santa Cruz, CA) with protease inhibitor cocktail (#P8340; Sigma-Aldrich) and phosphatase inhibitor cocktail (#P0044; Sigma-Aldrich) and Western blotting analysis was performed as we previously described[54]. Briefly, cell lysates were denatured by boiling the sample at 95° C. for 5 min and resolved by SDS-PAGE. Proteins were transferred to Amersham Hybond-P polyvinylidene difluoride (PVDF) membrane (#10600023; GE Healthcare Life Sciences, Germany) and blocked with 5% non-fat milk in TBS buffer with 0.1% Tween-20 (TBST) at room temperature for 1 hour. The membranes were then sliced according to the molecular weights and incubated with primary antibodies at 4° C. overnight, washed with TBST, and incubated with horseradish peroxidase (HRP)-conjugated secondary antibodies at room temperature for 2 hours. Signals were detected by SuperSignal™ West Pico PLUS Chemiluminescent Substrate (#34579; Thermo Fisher Scientific). The primary antibodies, including anti-TERT (H-231), anti-BRAF (F-7), anti-ERK (K-23), anti-GABPA (H-180), anti-GABPB (E-7), anti-c-FOS (H-125), anti-phospho-c-FOS (34E4), anti-MYC (9E10), and anti-β-actin (C-4) were purchased from Santa Cruz Biotechnology (Santa Cruz, CA). The anti-phospho-ERK1/2 (Thr202/Tyr204) antibody was purchased from Cell Signaling Technology (Beverly, MA). HRP-linked secondary antibodies, including anti-mouse IgG (#7076S) and anti-rabbit IgG (#7074S), were purchased from Cell Signaling Technology.

Transient TERT or MYC Knockdown.

TERT siRNA (#sc-36641) and negative control siRNA (#sc-37007) were purchased from Santa Cruz Biotechnology. MYC esiRNA (#EHU021051) and esiRNA targeting EGFP (negative control, #EHUEGFP) were purchased from Sigma-Aldrich. These siRNA were transfected to cells using Lipofectamine RNAiMAX Reagent (Invitrogen) according to the manufactory's protocol. Cells were harvested two days after transfection and the knockdown efficiency was determined by Western blotting. Transfected cells were subjected to functional analyses.

Transient FOS and FOS Mutant Overexpression.

The wild-type FOS cDNA clone was purchased from Origene (#SC116873, OriGene Technologies Inc., Rockville, MD, USA). To construct FOS mutant to prevent phosphorylation, FOS clone containing alanine replacements on Thr-232, hr-325, Thr-331, and Ser-374, was generated by the QuikChange Lightning Site-Directed Mutagenesis Kit (#210518, Stratagene, La Jolla, CA). The primer sequences used for mutagenesis are listed in Table 1. The FOS wild-type and FOS mutant plasmids were transfected into KAT18 cells using Lipofectamine 3000 (Invitrogen) according to the manufactory's protocol.

Stable Knockdown of BRAF.

TERT. FOS or MYC in cells. The short hairpin RNA (shRNA) specifically against BRAF and the scramble control shRNA were cloned into the lentiviral vector pSicoR-PGK-puro (#12084, Addgene, Cambridge, MA) as we previously described[55]. A pLKO.1-puro based lentiviral vector expressing shRNA against TERT (#TRCN0000240466), FOS (#TRCN0000016007) and MYC (#TRCN0000039642) were purchased from Sigma-Aldrich and the pLKO.1-puro vector with scramble shRNA was purchased from Addgene (plasmid #1864). To generate lentiviral particles, the lentiviral shRNA-expressing vector with the packaging plasmid PSPAX2 and the VSV-G envelope protein-coding plasmid pMD2.G were co-transfected to HEK293T cells using Lipofectamine 3000 (Invitrogen) and the supernatant was harvested 48 hours after transfection. To generate cell lines with stable knockdown of BRAF, TERT, FOS or MYC, cancer cells were exposed to the above lentivirus-containing supernatant for 24 hours in the presence of 8 μg/ml polybrene (Millipore, Billerica, MA) and selected by 2 μg/ml puromycin (Sigma-Aldrich) for 2 weeks. The stable transfection cell pools were confirmed by Western blotting analysis of the proteins of interest.

Introduced BRAF V600E Overexpression.

The pBabe-Puro-BRAF-V600E plasmid (Addgene plasmid #15269) was used for introduced overexpression of BRAF V600E in cells that naturally did not harbor BRAF V600E mutation. The BRAF WT was generated from plasmid carrying the V600E mutation (T1799A) using the QuikChange Lightning Site-Directed Mutagenesis Kit (Stratagene, La Jolla, CA) with primers listed in Table 1. Retroviral particles were produced by co-transfecting HEK293T cells with the pBabe-Puro-BRAF-V600E or pBabe-Puro-BRAF-WT plasmid, the packaging plasmid pUMVC, and the envelope plasmid pCMV-VSV-G as described previously[56]. The WRO cells were infected with a mixture of retrovirus and polybrene (Millipore) and cell pools with stable transfection were selected by puromycin (Sigma-Aldrich).

Luciferase Reporter Gene Construct and Reporter Gene Assay.

To create the luciferase reporter gene construct containing the TERT promoter, the wide-type core promoter region of TERT, −288 to +61 from the ATG start site, was PCR-amplified from genomic DNA of normal human thyroid cell-derived HTORI-3 cells containing the wild-type TERT promoter. The PCR product was ligated into the pGL3-Basic luciferase vector (Promega, Madison, WI). The resulting plasmid was named p-TERT-WT. This luciferase reporter construct containing the wild-type TERT promoter was induced to contain TERT promoter mutation C228T or C250T by changing the corresponding C allele to T allele using the QuikChange Lightning Site-Directed Mutagenesis Kit (Stratagene). The resulting plasmids were named p-TERT-C228T and p-TERT-C250T, respectively.

A portion of the GABPA promoter (−620 to +268 from the transcription start site) was amplified using genomic DNA and cloned into the pGL3-Basic luciferase vector (Promega). Similarly, the GABPB promoter (−281 to +262 from the transcription start site) was cloned into pGL3-Basic vector. The mutations at the potential FOS and MYC binding sites were generated using the QuikChange Lightning Site-Directed Mutagenesis Kit (Stratagene). The primers used for cloning and mutagenesis are listed in Table 1.

For promoter activity assay, cells were seeded in triplicate into a 24-well plate and then transfected with 300 ng pGL3 plasmids containing the TERT, GAPBA, or GABPB promoter, together with 12 ng *Renilla* luciferase (pRL-TK) plasmid (normalizing control) using Lipofectamine 3000 (Invitrogen). At 24 hours after the transfection, cells were lysed and luciferase activities were measured using the Dual-Luciferase Reporter Assay System (Promega). Results were presented as relative luciferase activities, which were obtained by dividing firefly luciferase values with *Renilla* luciferase values for each set of reading.

Chromatin Immunoprecipitation (ChIP) Assay.

The ChIP assay was performed according to the protocol for the fast ChIP method[57]. Briefly, cells were cross-linked with 1% formaldehyde for 10 min, followed by incubation with 125 mM glycine for 5 min at room temperature. Cells were then lysed and sonicated 7 times for 15 seconds with 45 seconds rest between pulses at 40% pulse power using a Branson 150D Sonifier Liquid Processor (Branson Ultrasonic Corporation, Danbury, CT). The cross-linked protein/DNA was incubated with anti-FOS, anti-MYC, anti-GABPA, or anti-GABPB antibodies, or non-specific IgG overnight at 4° C. and purified by Protein A/G PLUS-Agarose (sc-2003, Santa Cruz Biotechnology). The precipitated DNA fragments were isolated with Chelex 100 resin (Bio-Rad Laboratories, Hercules, CA) and subjected to PCR amplification of the GABPB promoter region and the mutation-containing region of the TERT promoter using the primers listed in Table 1.

Co-Immunoprecipitation (Co-IP).

Cells were cultured in 100 mm cell culture plates, and lysed in 2.0 ml cold RIPA buffer (sc-24948; Santa Cruz Biotechnology) with protease and phosphatase inhibitors (#P0044; Sigma-Aldrich). Lysates were centrifuged at 10,000 g for 10 min at 4° C. and the supernatant was collected. For each immunoprecipitation, a 0.9 ml aliquot of lysate was incubated with 0.5-1.0 ug of the indicated antibody for 1 h at 4° C. and the resulting immuno-complex was pulled down by incubating with 25 ul Protein A/G Plus-Agarose (#sc-2003, Santa Cruz Biotechnology) overnight at 4° C. with rotation. The beads were washed four times with 1.0 ml cold lysis buffer, boiled in SDS sample buffer at 95° C. for 5 min, and subjected to Western Blot analysis using appropriate antibodies.

Cell Proliferation and Colony Formation Assays.

For cell proliferation assay, cells (800/well) were seeded on a 96-well plate and MTT assay was carried out daily over a 5-day course to evaluate cell proliferation as previously described[58]. For colony-formation assay, $1 \times 10^3$ K1 cells or $5 \times 10^3$ BCPAP cells were plated in triplicate on a 6-well plate with a bottom layer of 0.7% agar and atop layer of 0.35% agar. The total number of colonies ≥100 μm in diameter was counted and representative areas were photographed under a microscope after 3 weeks of culture.

Cell Migration and Invasion Assays.

Cell migration and invasion assays were performed in triplicates using Transwells in 24-well plates. Transwells with 8-μm pore polycarbonate membrane used for cell migration assay were obtained from Corning (Corning, NY). Transwells coated with Matrigel on the upper surface used for invasion assay were obtained from BD Biosciences (Franklin Lakes, NJ). Cells ($2 \times 10^4$ for migration assay; $5 \times 10^4$ for invasion assay) suspended in 250 μl of serum-free medium were placed in the upper chamber, while the lower chamber was loaded with 750 μl of cell culture medium with 10% FBS. After 24 hours of incubation, the non-invaded cells were removed from the upper surface by a cotton swab. The invaded cells on the lower surface of the membrane were fixed in 100% methanol for 15 min, air-dried, and stained with 0.1% crystal violet. Cells from three microscopic fields were photographed and counted.

Xenograft Tumorigenicity Assay.

All animal experiments were approved and performed according to the guidelines of the Institutional Animal Care and Use Committee (IACUC) of Johns Hopkins University. Four-weeks-old female nude mice (Hsd:Athymic Nude-Foxn1$^{nu}$ mice) were purchased from Harlan Laboratories (Frederick, MD). K1 ($1 \times 10^7$) cells stably expressing scramble shRNA or TERT shRNA were injected subcutaneously into the flanks of nude mice (10 mice per group). At two weeks of cell inoculation when the tumors in the control group approached about 150 mm$^3$, each group of animals were divided further into 2 subgroups (5 mice per subgroup) and treated daily with vehicle (5% DMSO, 1% methylcellulose) or 10 mg/kg PLX4032 by oral gavage. Tumor size was measured twice a week on the skin surface of the animal using a caliper and tumor volume was calculated using the formula (width$^2$×length)/2 as previously described. At the end of 4 weeks after cell inoculation, mice were scarified and tumors were surgically removed, photographed, and weighted.

Statistics

Two-tailed Student's t-test was used to determine the significance of difference between two groups in the assays of MTT, cell migration and invasion, colony formation in soft agar, luciferase reporter gene assay, qRT-PCR, and tumor formation in nude mice. For cell migration and invasion assay, colony formation assay, luciferase reporter assay, and qRT-PCR, three independent experiments were carried out, and each was done in triplicate. All the Western blotting, Co-IP, and ChIP assays were reproduced at least twice independently with similar results. All P values (Sudent's t-test) were two-sided and P<0.05 was considered significant. Analyses were performed using Stata (Stata/SE version 12 for windows; Stata Corp, College Station, Texas, USA) and GraphPad Prism (version 6 for Windows; GraphPad Software, Inc., San Diego, CA, USA).

Results

Cooperative Role of BRAF V600E and TERT in Cell Oncogenesis.

Figure 1B:
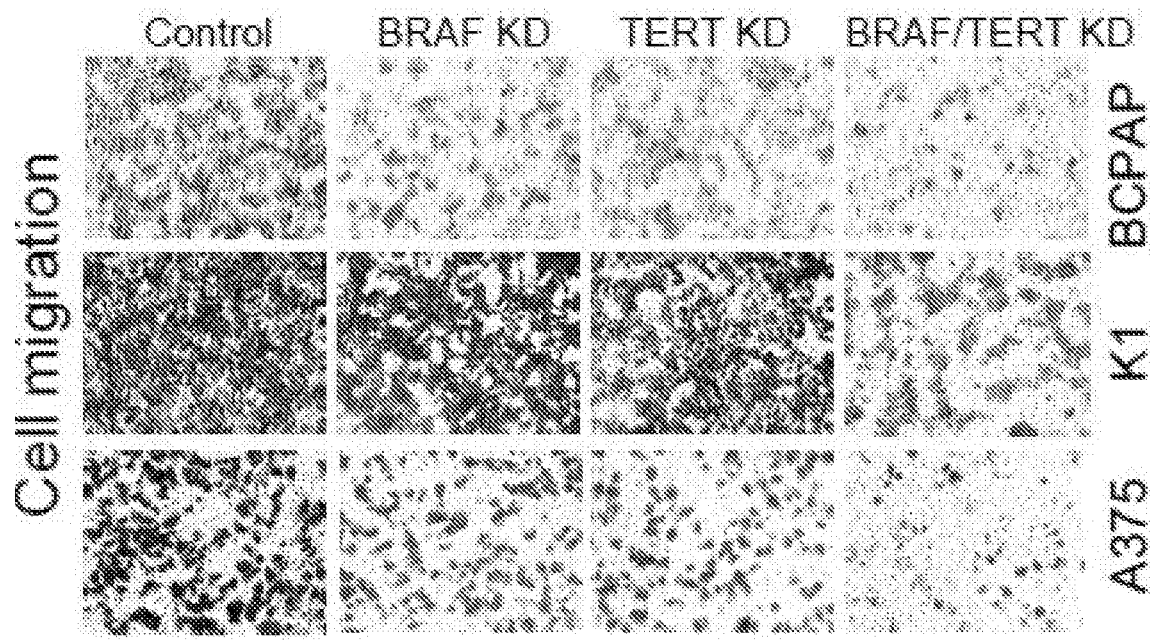
Figure 1C:
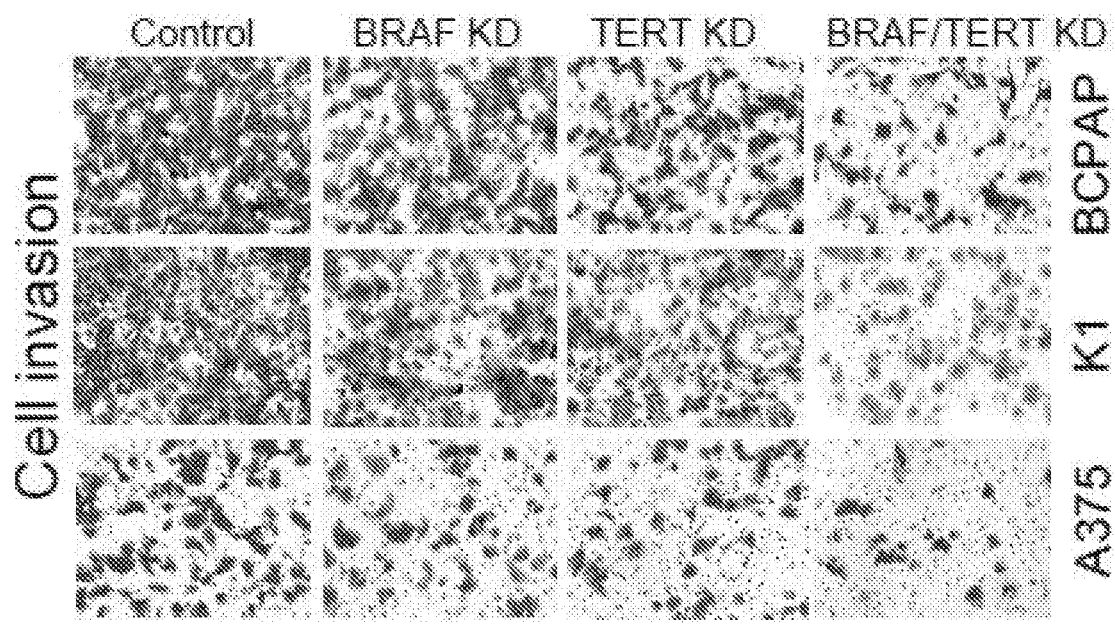
Figure 1D:
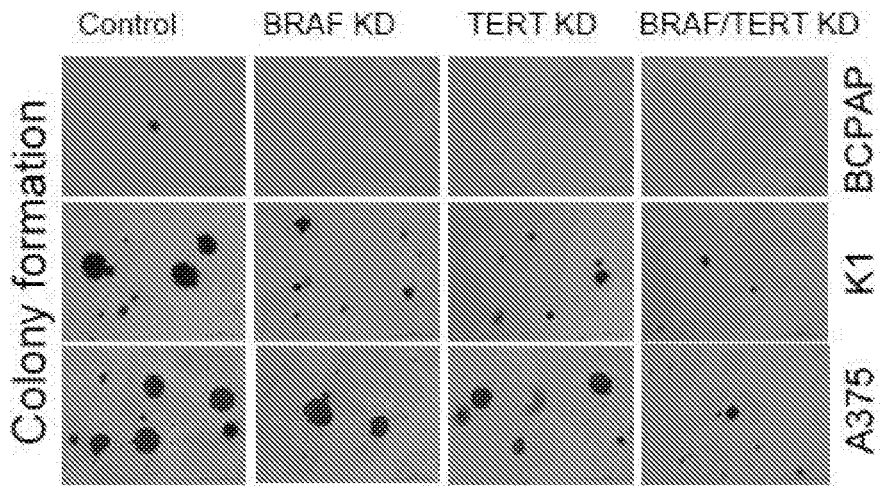
Figure 1E:
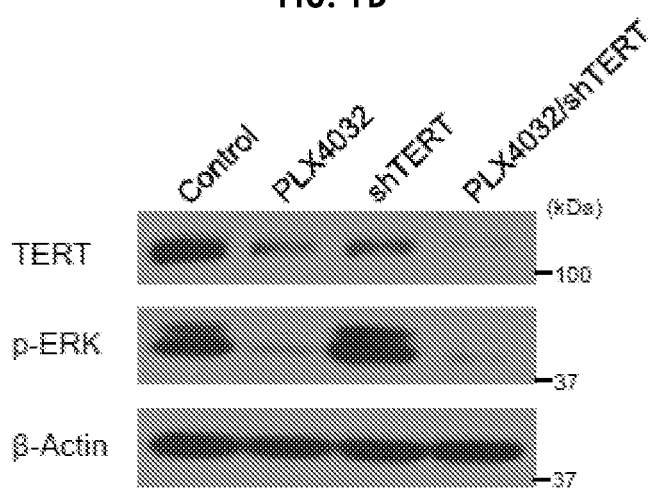
Figure 1F:
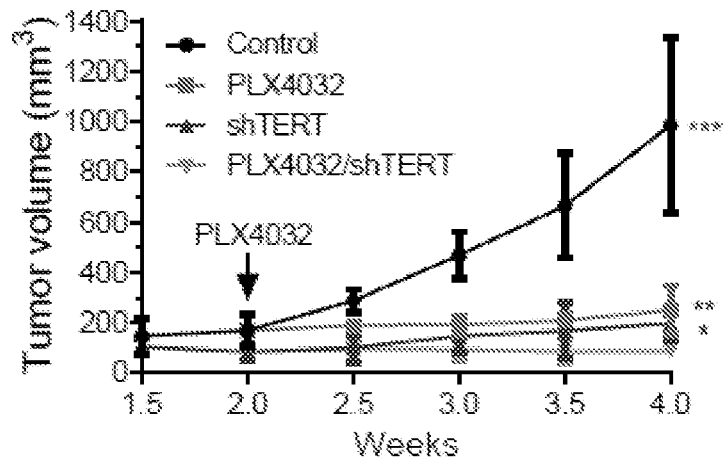
Figure 1G:
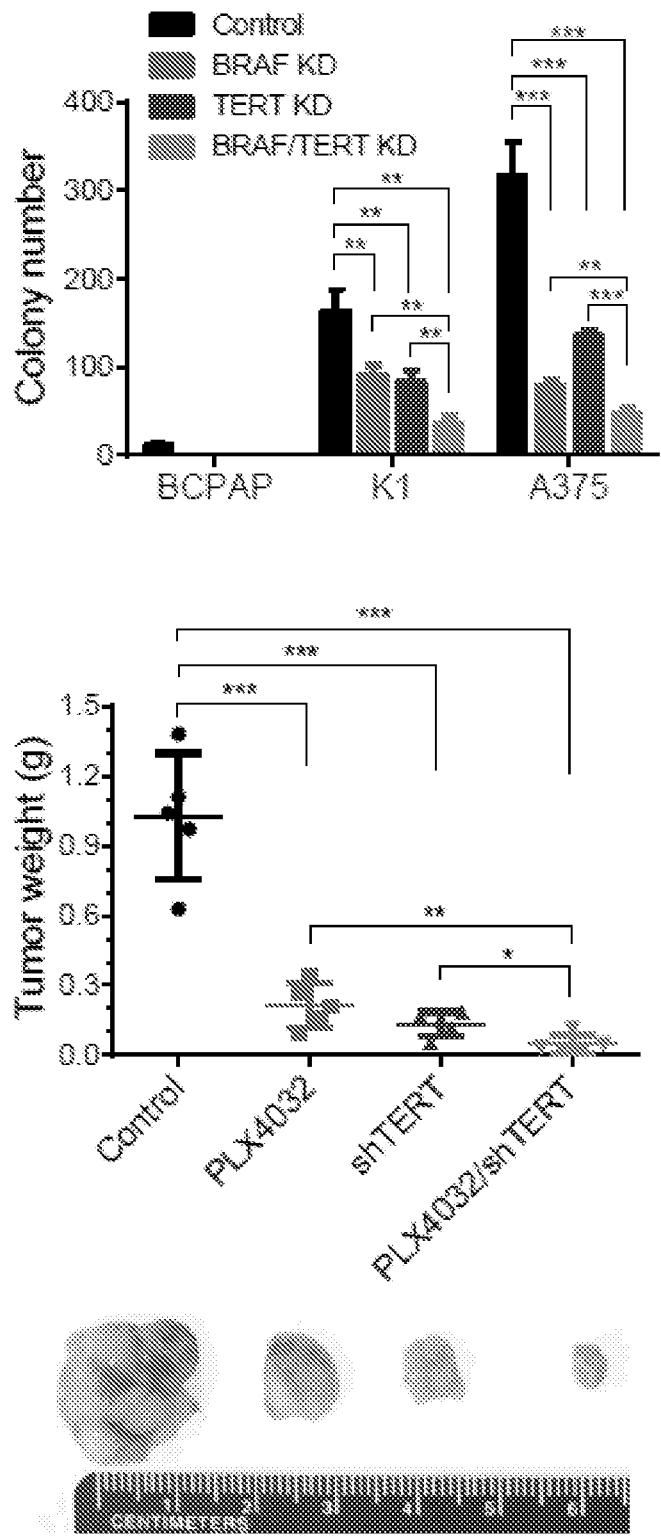
Figure 8:
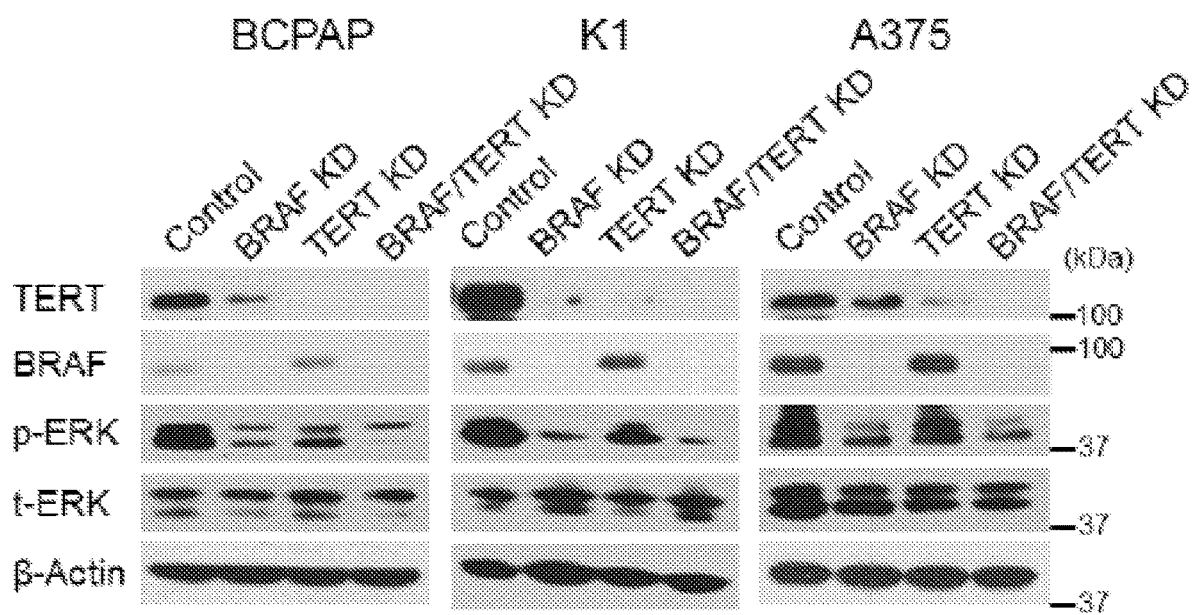
FIG. 8. Western blotting analyses of TERT, BRAF, phosphorylation of ERK (p-ERK), total ERK (t-ERK), and beta-Actin. Control scramble shRNA- or BRAF shRNA-expressing cells were co-transfected with control siRNA or TERT siRNA to also knockdown (KD) TERT.

To support the clinical findings on the genetic duet of BRAF V600E and TERT promoter mutations and demonstrate its biological relevance, we used in vitro and in vivo models to examine the roles of BRAF V600E and TERT in oncogenic cellular activities and xenograft tumor development of PTC cells BCPAP and K and melanoma cells A375, which all harbored both BRAF V600E and TERT promoter mutations. As shown in FIG. 8, BRAF shRNA effectively knocked down BRAF protein and suppressed ERK phosphorylation of the MAPK pathway; similarly, TERT siRNA knocked down more than 80% of TERT protein in the three cells. Knockdown of either BRAF or TERT significantly inhibited cell proliferation and dual knockdown of BRAF and TERT induced a further inhibition (FIG. 1A). Either BRAF or TERT knockdown decreased cell migration and invasion and dual knockdown of BRAF and TERT had more robust effects (FIGS. 1B and 1C). Similarly, either BRAF or TERT knockdown inhibited anchorage-independent growth of K1 and A375 cells in soft agar and dual knockdown of BRAF and TERT nearly completely abolished colony growth (FIG. 1D). BCPAP cells naturally formed only a few colonies in soft agar and knockdown of either BRAF or TERT completely abolished the colony formation (FIG. 1D). We also tested the role of BRAF V600E and TERT in thyroid tumor growth using the BRAF V600E inhibitor PLX4032 and stable TERT knockdown to suppress the MAPK pathway and the TERT, respectively, in K1 cell (FIG. 1E), from which xenograft tumors were derived (FIGS. 1F and 1G). Either administration of PLX4032 or TERT knockdown inhibited tumor growth and combination of the two nearly completely abolished tumor growth (FIGS. 1F and 1G), particularly evident in tumor weight (FIG. 1G). These data demonstrated that, like BRAF V600E, TERT also played a robust role in cancer-hallmark oncogenic cellular activities and tumorigenesis of cancer cells; the oncogenic effect of TERT was in fact even more robust than BRAF V600E in these cells harboring both BRAF V600E and TERT promoter mutations. TERT was thus demonstrated here to be a powerful oncoprotein. These results also showed that BRAF V600E and TERT displayed a cooperative manner in promoting the oncogenic behaviors of these cells, recapitulating the clinical findings on the genetic duet of BRAF V600E and TERT promoter mutations.

BRAF V600E and TERT Mutation Cooperatively Upregulated TERT.

Figure 2A:
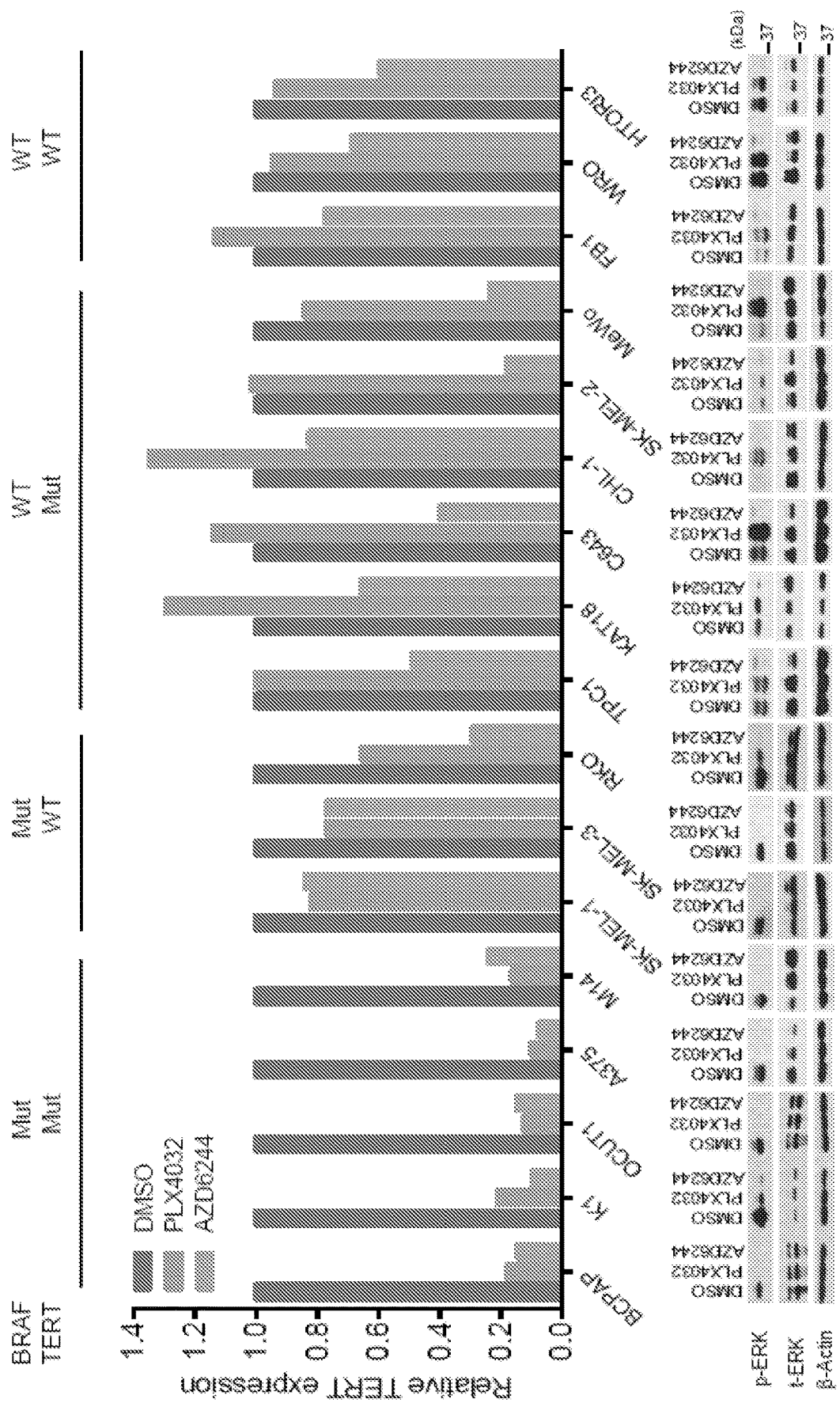
FIG. 2A-2G. BRAF V600E/MAPK pathway regulated TERT expression.
Figure 9A:
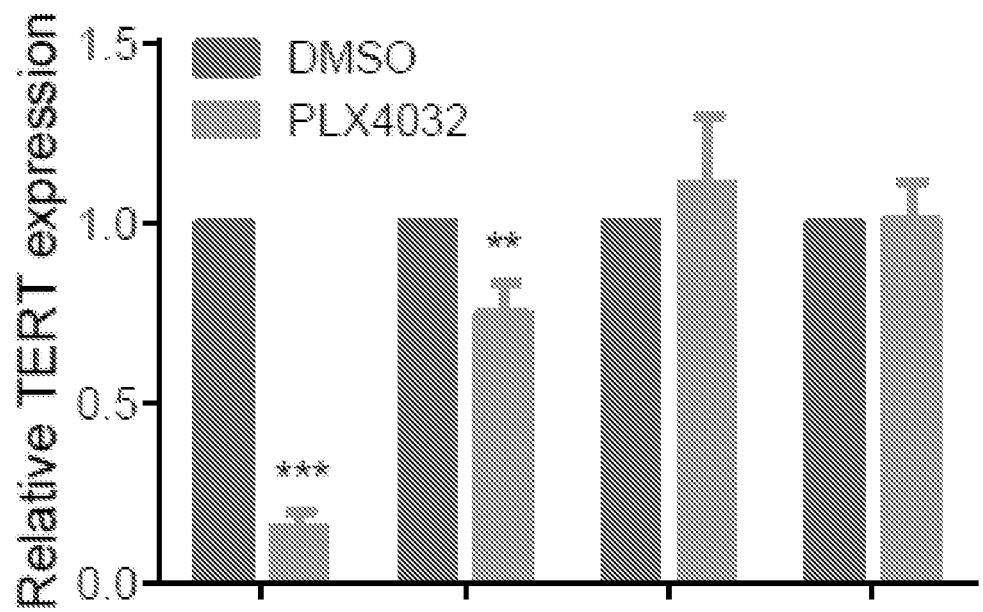
FIG. 9A-9B. Summarized effects of PLX4032 (FIG. 9A) and AZD6244 (FIG. 9B) on TERT mRNA expression. Each bar represents the average+SD of the cells with the same genotypes as follows: BRAF-mut and TERT-mut cell lines: BCPAP, K1, OCUT1, A375, and M14; BRAF-mut and TERT-wt cell lines: SK-MEL-1, SK-MEL-3, and RKO; BRAF-wt and TERT-mut cell lines: TPC1, KAT18, C643, CHL-1, SK-MEL-2, and Mewo; BRAF-wt and TERT-wt cell lines: FB1, WRO, and HTORI3. Compared with the corresponding control of DMSO, P<0.01, *P<0.001, by independent t-test.
Figure 9B:
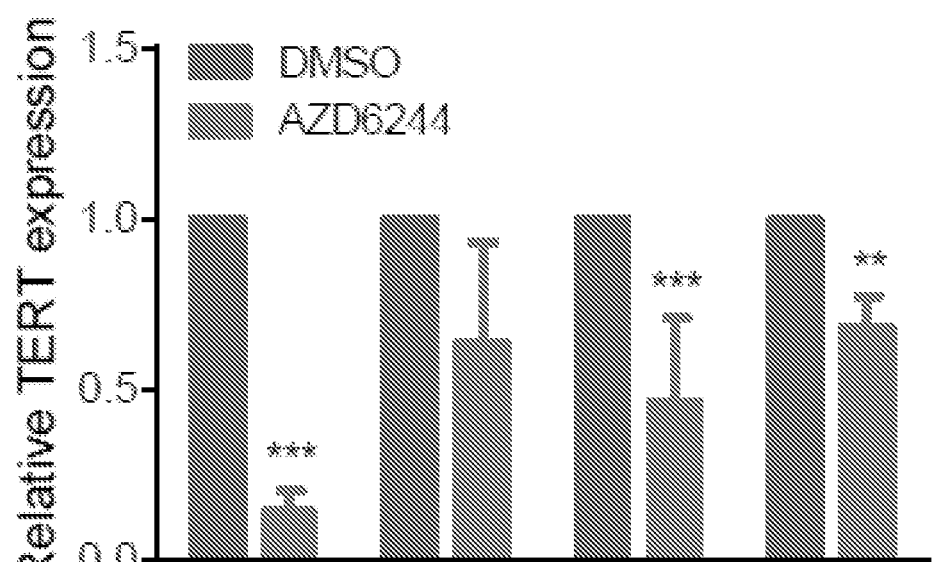
Figure 10A:
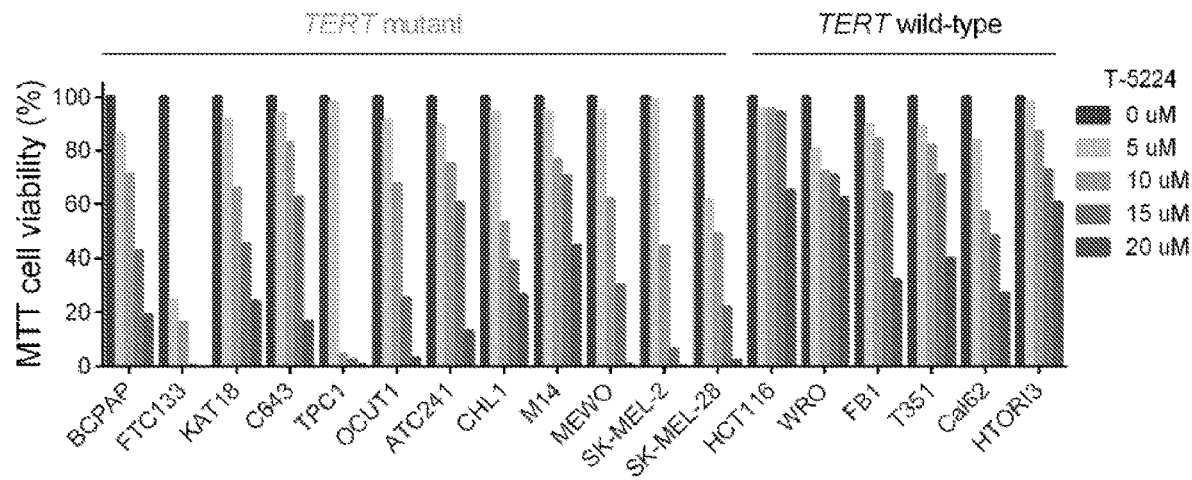
FIG. 10A-10B. Effect of FOS inhibitor T-5224 on cell growth.
Figure 10B:
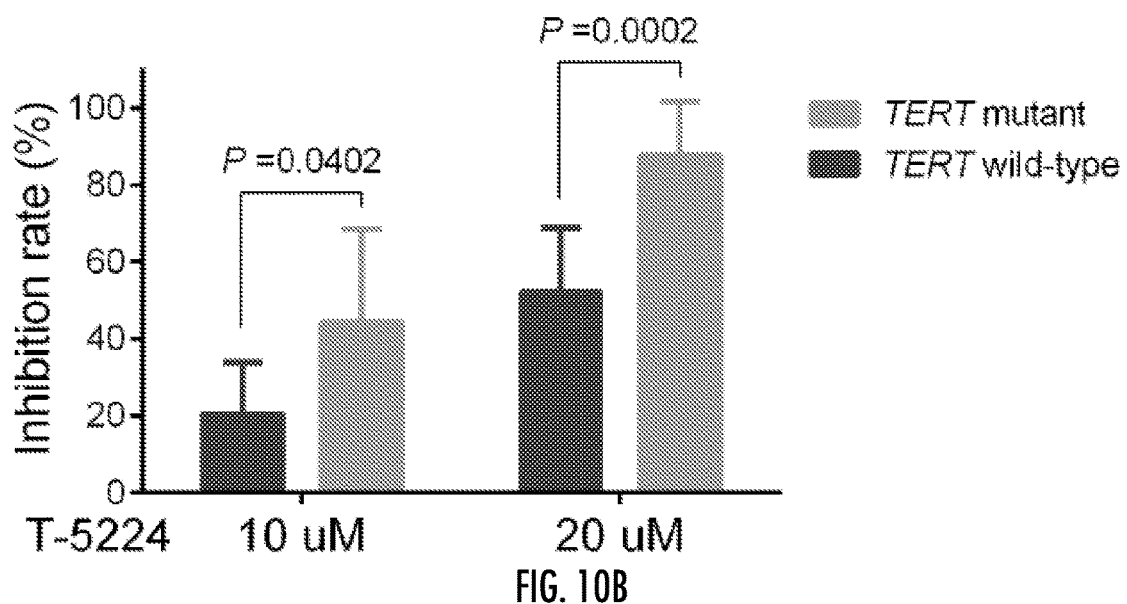

We next investigated whether BRAF V600E and TERT promoter mutations cooperatively affected TERT expression in a panel of human cancer cells with various BRAF and TERT genotypes (Table 2). The BRAF V600E inhibitor PLX4032 specifically suppressed ERK phosphorylation in cells harboring BRAF V600E mutation and dramatically inhibited TERT expression in cells harboring both BRAF V600E and TERT promoter mutations, but had limited effect on TERT expression in cells harboring the wild-type TERT promoter and had no inhibitory effect in cells harboring wild-type BRAF (FIG. 2A, FIG. 9A). In fact, several wild-type BRAF cell lines showed an increase in ERK phosphorylation after the treatment with PLX4032, consistent with the previous finding that PLX4032 induced MEK and ERK phosphorylation in wild-type BRAF cells[28, 29], correspondingly leading to an increase in TERT expression, especially in TERT mutant cells (KAT18, C643 and CHL-1) (FIG. 2A). The MEK inhibitor AZD6244 similarly inhibited TERT expression in cells harboring BRAF V600E mutation, while it had a modest inhibitory effect on ERK phosphorylation in cells harboring wild-type BRAF and, in such cells, it inhibited TERT expression more in those harboring TERT promoter mutations (FIG. 2A, FIG. 9B).

TABLE 2

Genotypes of BRAF and TERT genes in various human cancer cell lines.

| Cell Line | BRAF | TERT Promoter | Derivation |
|---|---|---|---|
| BCPAP | V600E, homozygous | C228T/C229T, heterozygous | thyroid carcinoma |
| K1 | V600E, heterozygous | C228T, heterozygous | thyroid carcinoma |
| OCUT1 | V600E, heterozygous | C250T, homozygous | thyroid carcinoma |
| TPC1 | wildtype | C228T, heterozygous | thyroid carcinoma |
| KAT18 | wildtype | C228T, heterozygous | thyroid carcinoma |
| C643 | wildtype | C228T, heterozygous | thyroid carcinoma |
| FB1 | wildtype | wildtype | thyroid carcinoma |
| WRO | wildtype | wildtype | thyroid carcinoma |
| HTORI3 | wildtype | wildtype | thyroid epithelium |
| A375 | V600E, homozygous | C250T, heterozygous | melanoma |
| M14 | V600E, heterozygous | C250T, heterozygous | melanoma |
| SK-MEL-1 | V600E, heterozygous | wildtype | melanoma |
| SK-MEL-3 | V600E, heterozygous | wildtype | melanoma |
| SK-MEL-2 | wildtype | C250T, homozygous | melanoma |
| MeWo | wildtype | C250T, heterozygous | melanoma |
| CHL-1 | wildtype | C228T, heterozygous | melanoma |
| RKO | V600E, homozygous | wildtype | colon carcinoma |
| SW48 | wildtype | wildtype | colon carcinoma |

Figure 2B:
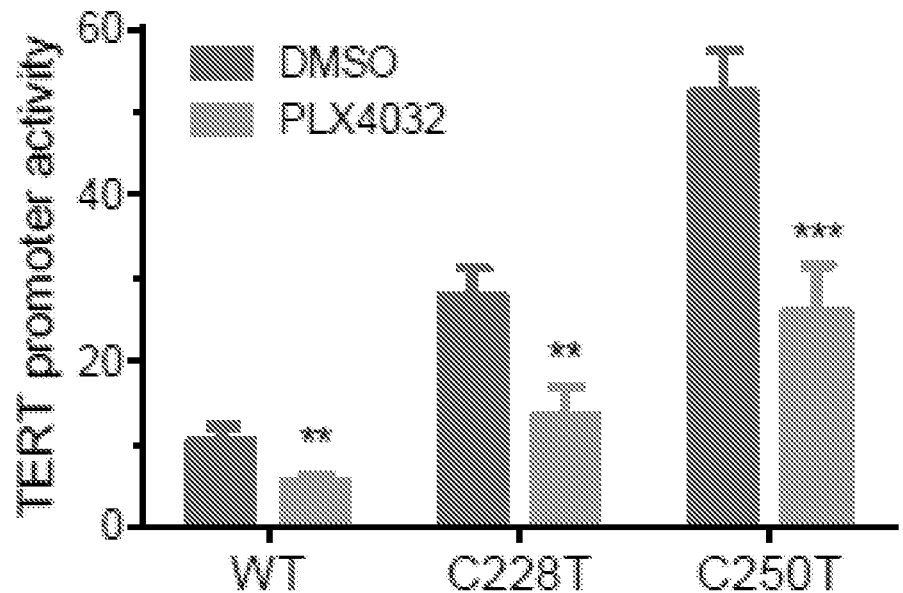
Figure 2C:
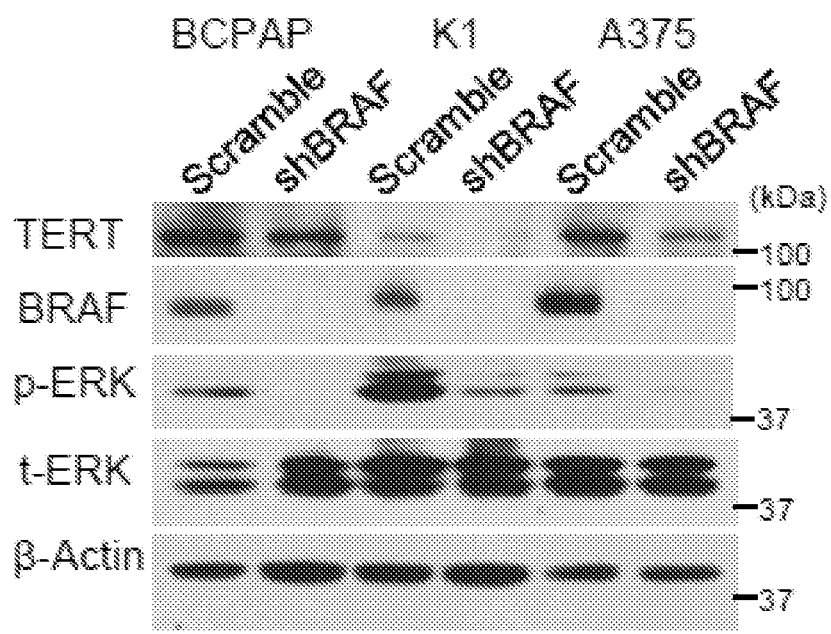
Figure 2D:
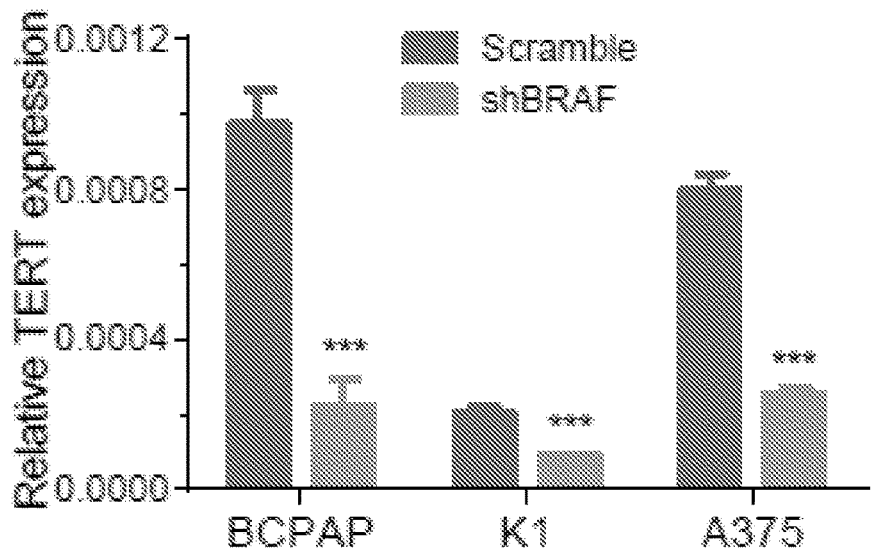
Figure 2E:
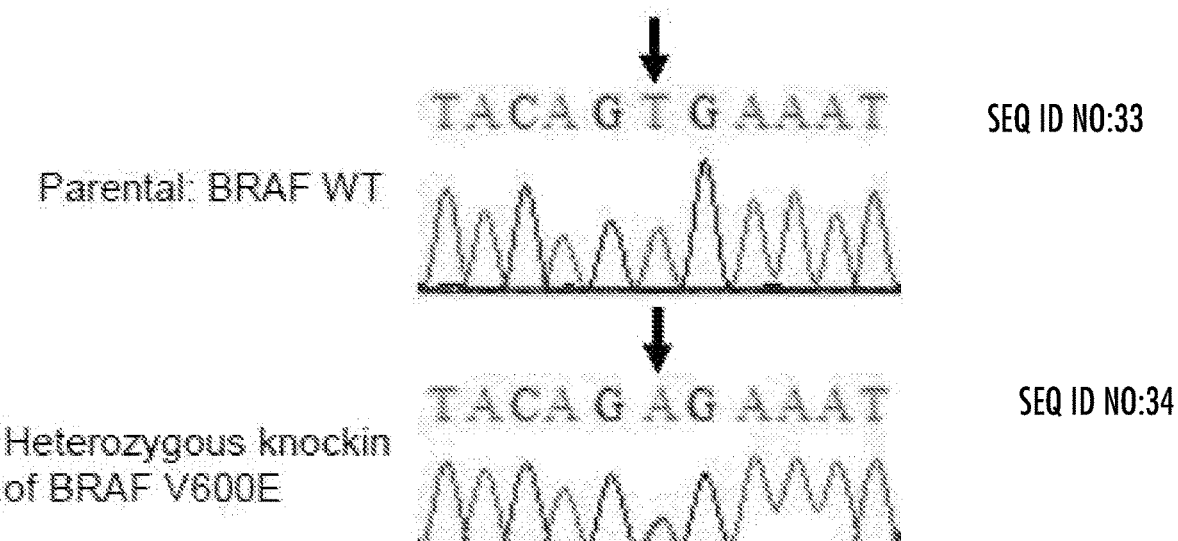
Figure 2F:
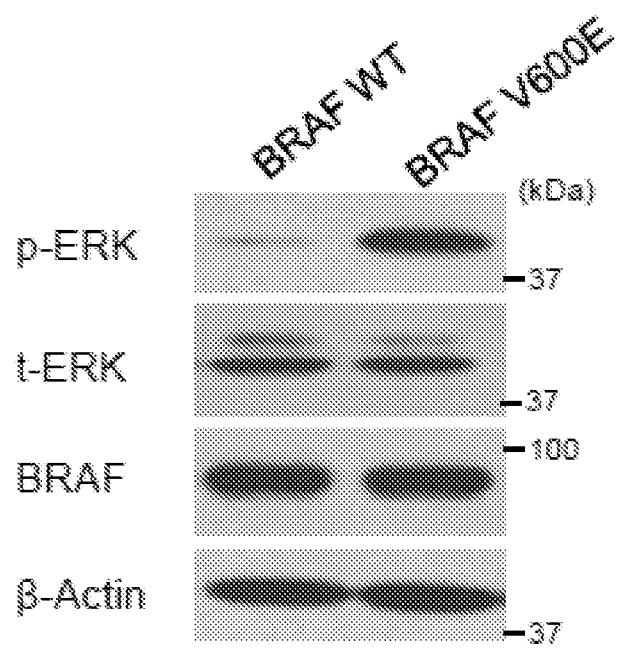
Figure 2G:
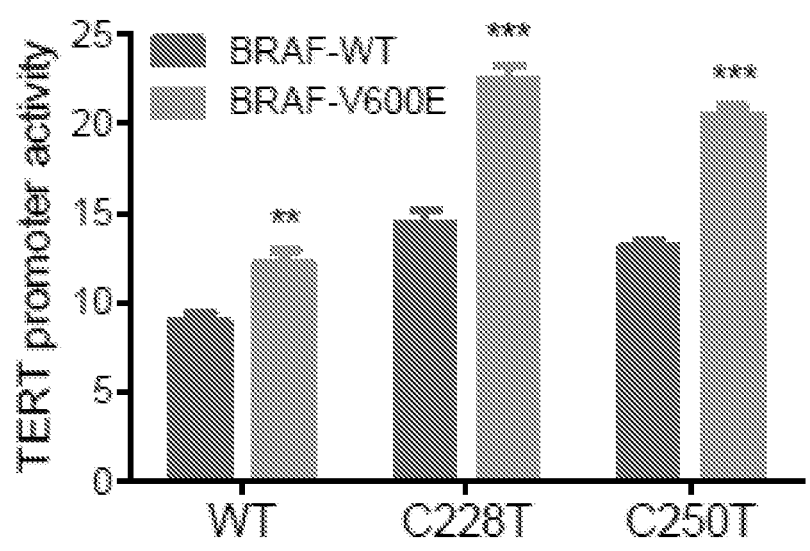

In luciferase reporter assay examining the effect of BRAF V600E on TERT promoter activities in K1 cells harboring BRAF V600E (FIG. 2b), TERT promoter was far more active when harboring the C228T or C250T mutation than the wild-type; treatment with PLX4032 dramatically reduced the activities of the mutated TERT promoter and has limited effect on the wild-type TERT promoter. To further confirm the role of BRAF V600E in TERT expression, we stably knocked down BRAF in BCPAP, K1 and A375 cells, resulting in significantly reduced expression of TERT in all these cells (FIGS. 2C and 2D). The somehow less pronounced decrease in TERT protein (FIG. 2C) than the decrease in TERT mRNA (FIG. 2d) in the BCPAP cell suggests that the protein translational synthesis system in this cell likely had a good efficiency at low levels of RNA. In contrast, BRAF V600E knock-in activated the MAKP pathway (FIGS. 2E and 2F) and increased the activities of TERT promoter, especially the mutant types (FIG. 2G). These results again demonstrated a TERT promoter mutation-dependent activation of the TERT gene by the BRAF V600E/MAPK pathway.

Mutation-Independent Activation of TERT by BRAF V600E Via MYC.

Figure 3A:
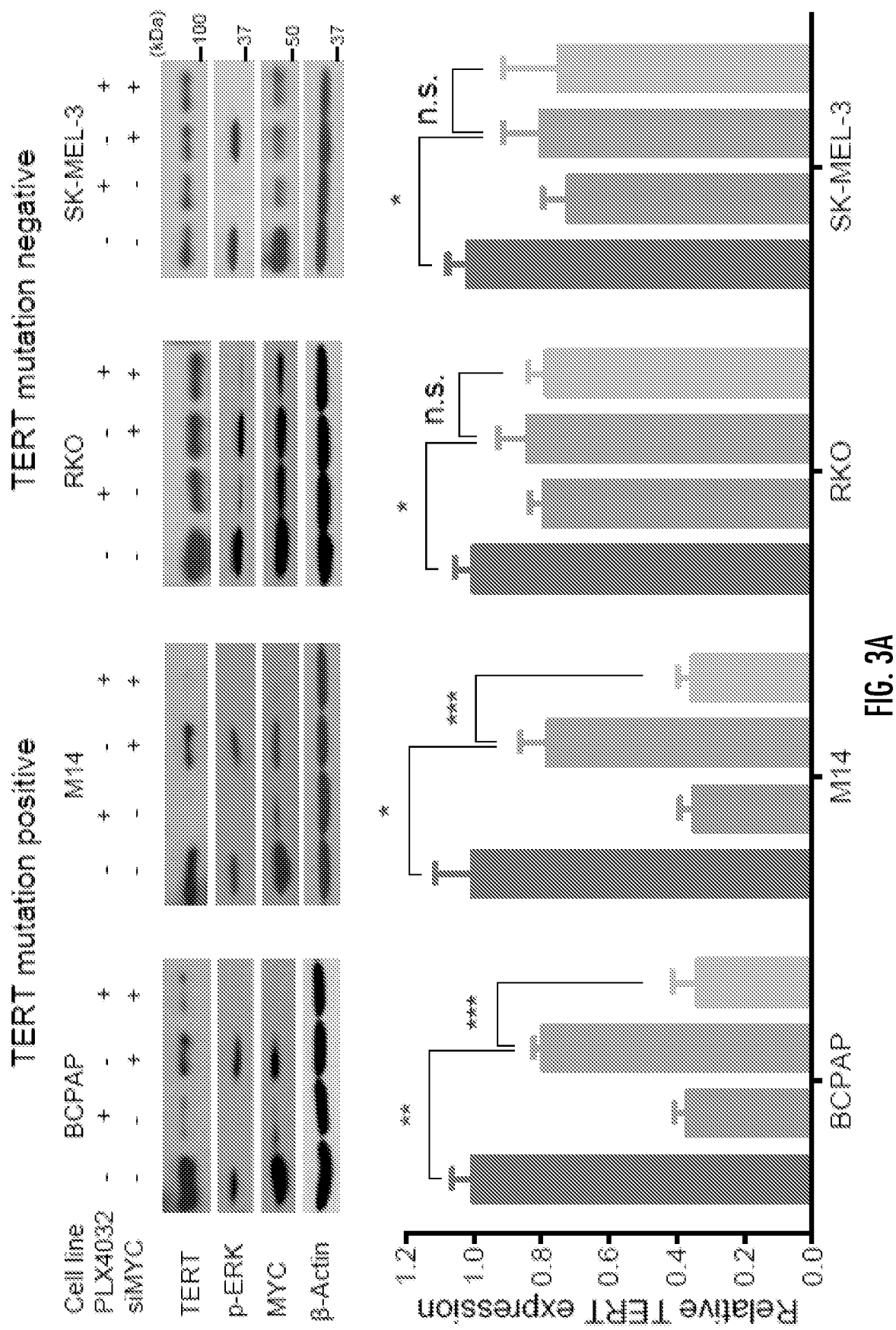
FIG. 3A-3C. MYC regulated TERT expression in a TERT promoter mutation-independent manner.
Figure 3B:
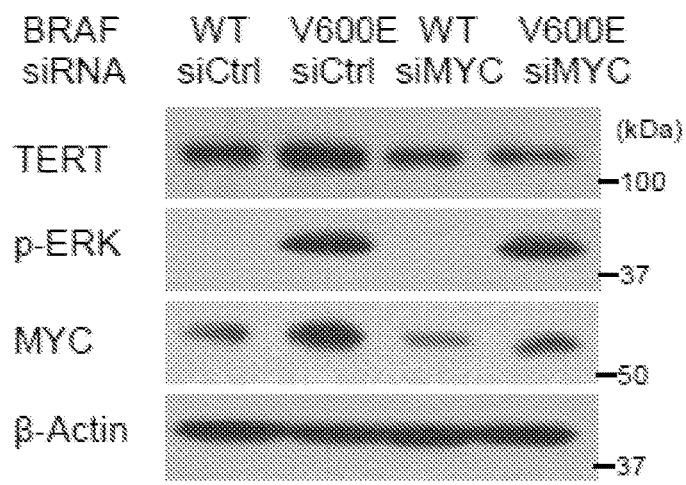
Figure 3C:
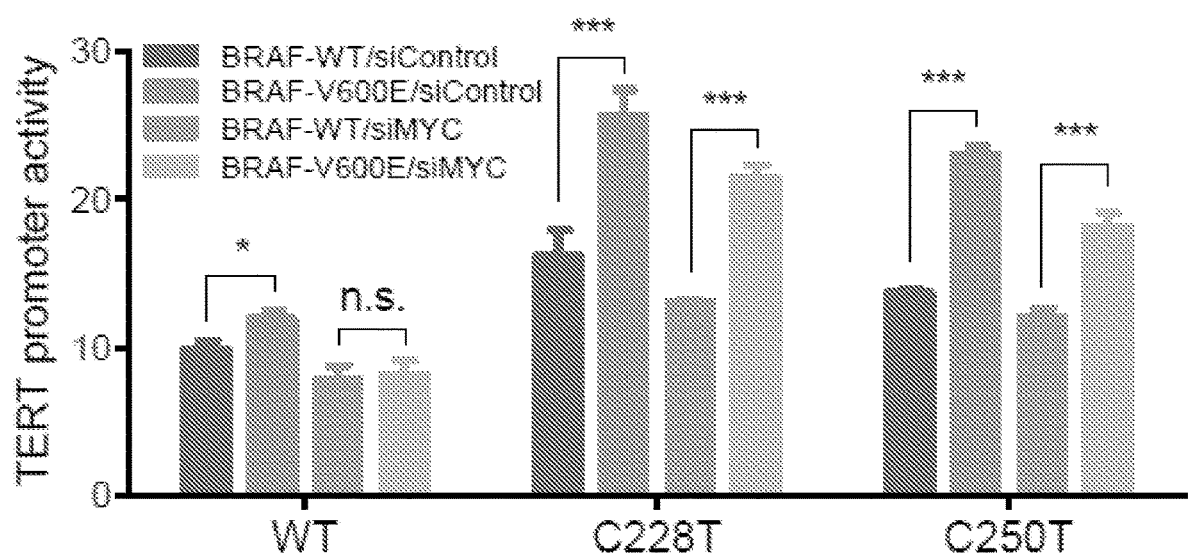

Since c-MYC was previously shown to activate TERT transcription by direct binding to TERT promoter[30], we investigated whether MYC played a role in mediating BRAF V600E-regulated TERT expression. Inhibition of BRAF V600E by PLX4032 suppressed MYC expression, associated with decreased TERT expression in all the cells harboring BRAF mutation (FIG. 3A), suggesting that MYC indeed played a role, albeit moderately, in BRAF V600E-regulated TERT expression. MYC knockdown inhibited TERT expression to a similar moderate level as PLX4032 did in RKO and SK-MEL-3 cells which harbored wild-type TERT promoter (FIG. 3A). PLX4032 could further inhibit TERT expression after siRNA knockdown of MYC in cells harboring TERT promoter mutations, but not in cells harboring wild-type TERT promoter (FIG. 3A). These data suggest that the TERT promoter mutation-dependent activation of the TERT promoter by the BRAF V600E/MAPK pathway was a more effective mechanism for the regulation of TERT than that by the MYC component and the latter was TERT promoter mutation-independent. BRAF V600E knock-in in wild-type TERT promoter cells increased MYC expression, which was associated with an increase in TERT expression; the latter increase was abolished by siRNA knockdown of MYC (FIG. 3B). These results provided further evidence that the TERT promoter mutation-independent component in the regulation of TERT by the BRAF V600E/MAPK pathway was MYC-mediated. We further showed that BRAF V600E knock-in in cells resulted in increased TERT promoter activities in a far more robust manner in the promoter harboring the C228T or C250T mutation than the wild-type TERT promoter (FIG. 3C). Mutant TERT promoter activities were still significantly increased by BRAF V600E knock-in in the presence of MYC knockdown, but the wild-type TERT promoter activity was not increased by BRAF V600E knock-in in the presence of MYC knockdown (FIG. 3C). These results again suggested that the MYC component in the regulation of TERT by the BRAF V600E/MAPK pathway was TERT promoter mutation-independent and was minor while the TERT promoter mutation-dependent component was dominant.

BRAF V600E Upregulated GABPB and GABP Binding to Mutant TERT.

Figure 4A:
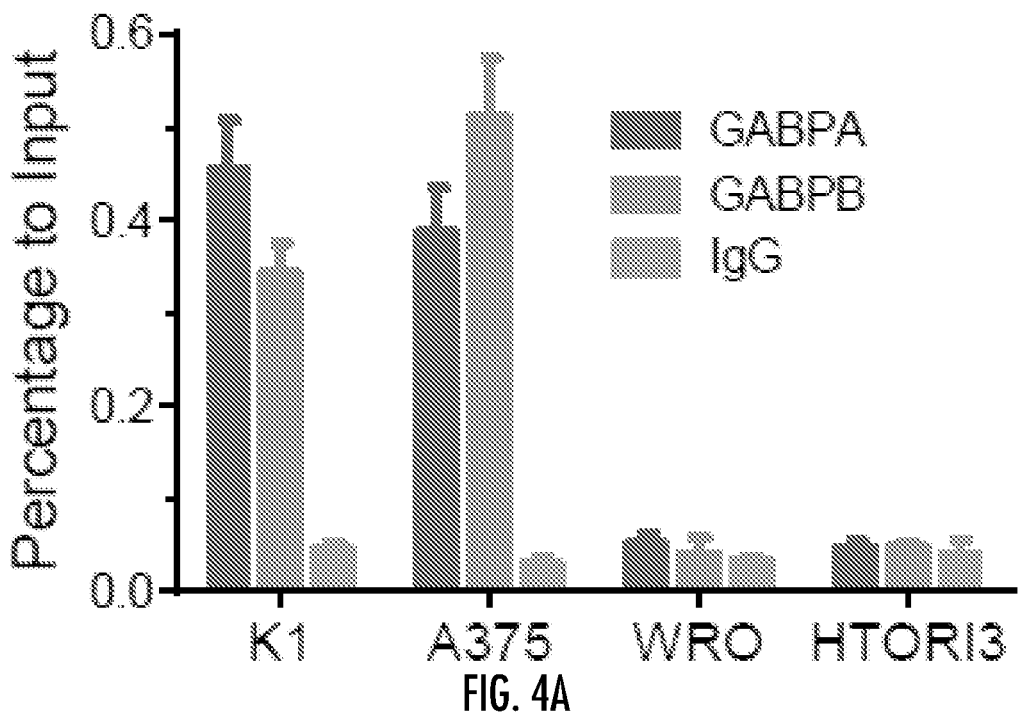
FIG. 4A-4E. BRAF V600E promoted GABP binding to mutant TERT promoter by upregulating GABPB.
Figure 4B:
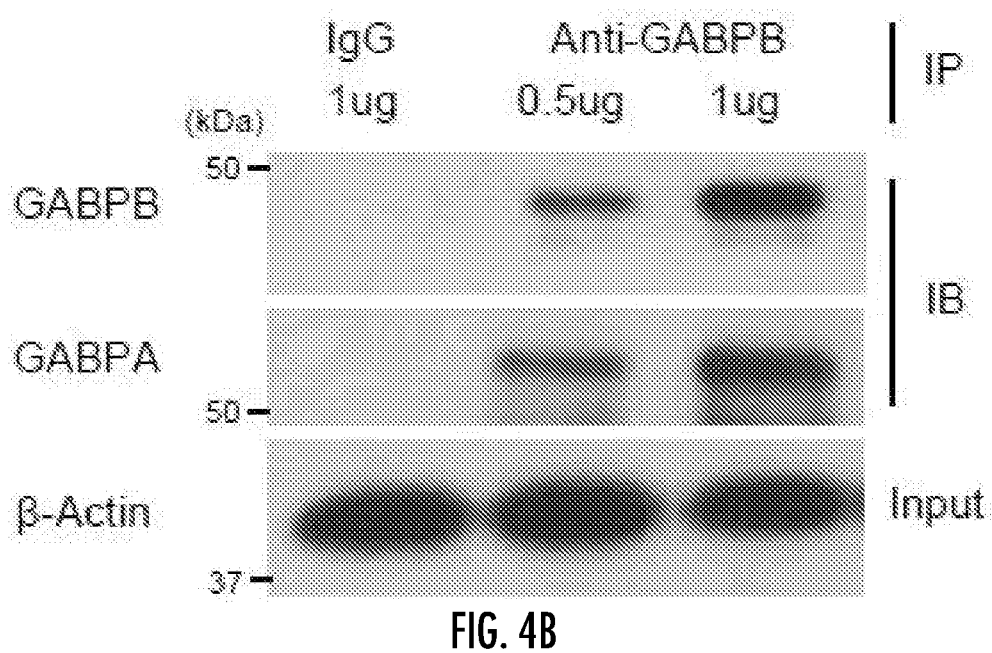
Figure 4C:
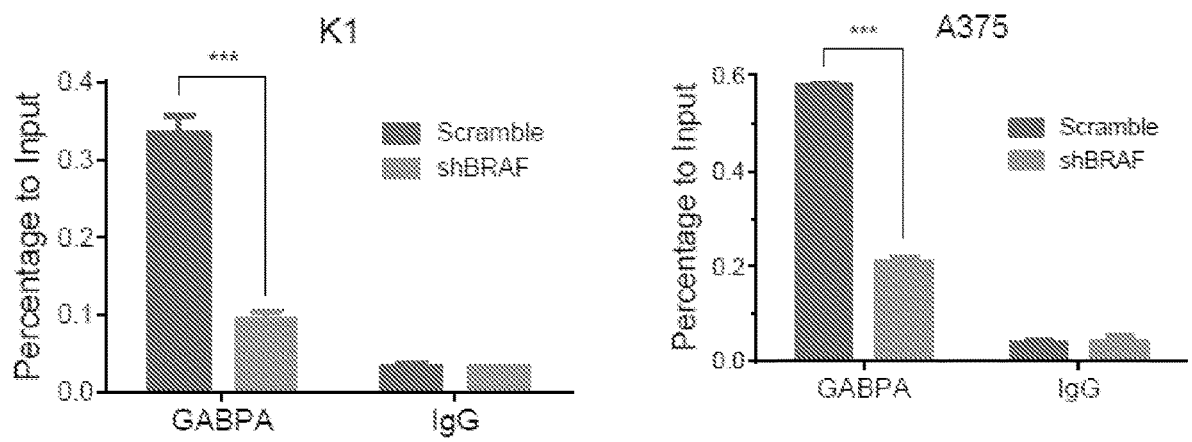
Figure 4D:
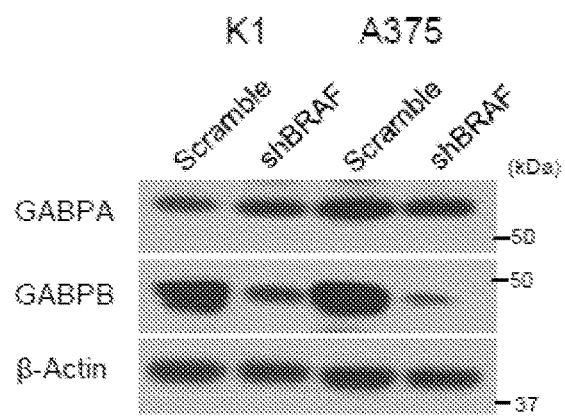
Figure 4E:
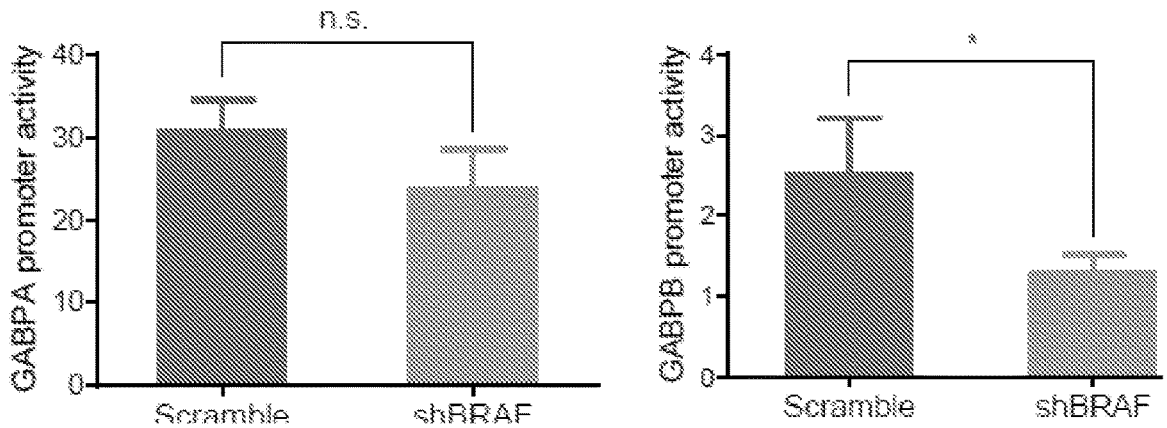

We next investigated how BRAF V600E and TERT promoter mutations synergistically activated TERT. It was recently demonstrated that the ETS transcription factor GABPA selectively bound and activated the mutant TERT promoter, but not the wild-type TERT promoter, in human cancer cells.[31, 32] We hypothesized that the BRAF V600E/MAPK pathway might regulate the GABP transcriptional machinery of TERT. To confirm the role of GABP in the regulation of mutant TERT in our cell systems, we demonstrated that, similar to GABPA, GABPB also bound to TERT promoter in cells harboring TERT promoter mutations, but not in cells harboring the wild-type TERT (FIG. 4A). Co-immunoprecipitation (Co-IP) assay revealed that GABPA and GABPB formed a complex in the cell (FIG. 4b), consistent with the notion that GABPA complexes with GABPB to form tetramers, creating a fully functional GABP complex that binds DNA and activates gene transcription.[33, 34, 35] We next investigated whether BRAF V600E/MAPK pathway regulated the binding of GABP to TERT promoter. Chromatin immunoprecipitation (ChIP) assay showed that BRAF knockdown decreased the binding of GABP to the mutant TERT promoter when anti-GABPA antibody was used in the assay (FIG. 4C). Interestingly, BRAF knockdown decreased the expression of GABPB, but not GABPA (FIG. 4D), suggesting that the BRAF V600E/ MAPK pathway selectively upregulated the GABPB gene, resulting in increased production of GABPB, which in turn drove the formation of the GABPA-GABPB transcriptional complex. To further support this concept, luciferase reporter assay showed that BRAF knockdown decreased the promoter activity of GABPB, but not that of GABPA (FIG. 4E). These results, taken together, demonstrate a mechanism in which by upregulating the expression of GABPB, the BRAF V600E/MAPK pathway promotes the formation of the GABPA-GABPB complex and consequent activation of the mutant TERT promoter, upregulating TERT expression.

FOS Activated the GABPB Gene by Directly Binding to its 5'-UTR Region.

Figure 5A:
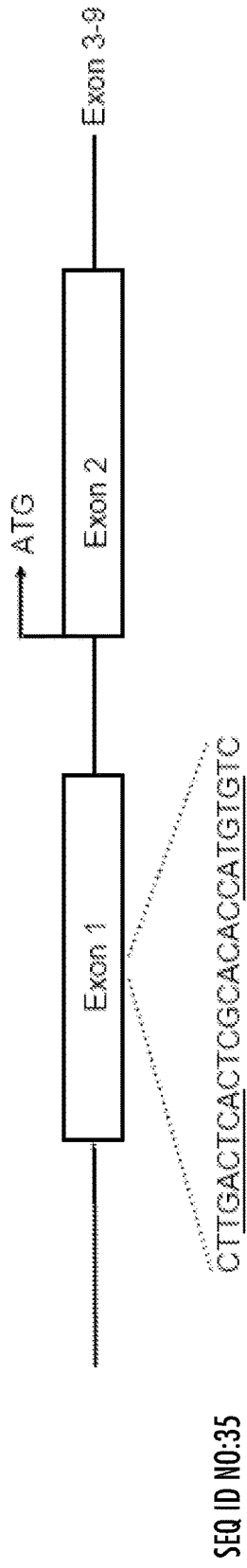
FIG. 5A-5F. FOS bound to 5'-UTR of GABPB and upregulated mutant TERT expression.
Figure 5B:
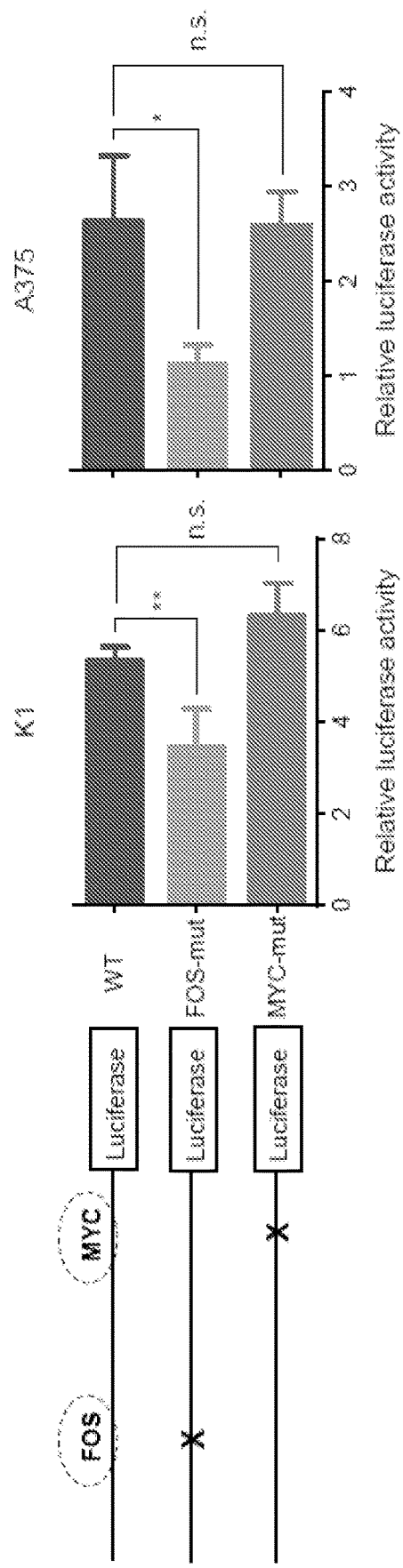
Figure 5C:
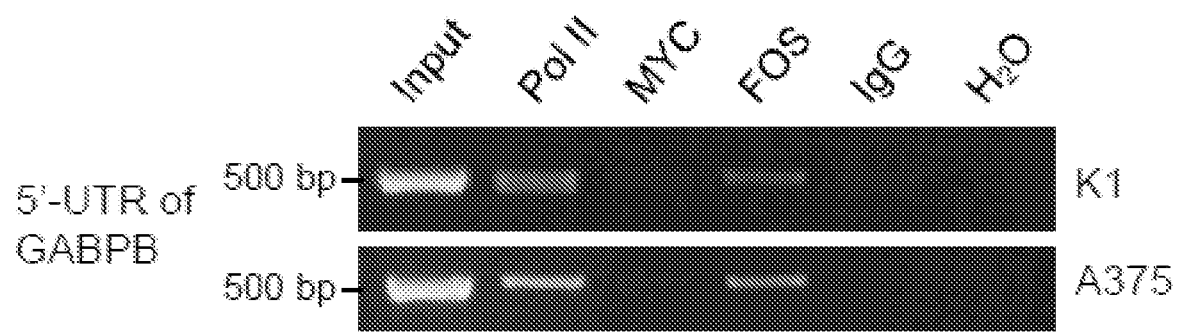
Figure 5D:
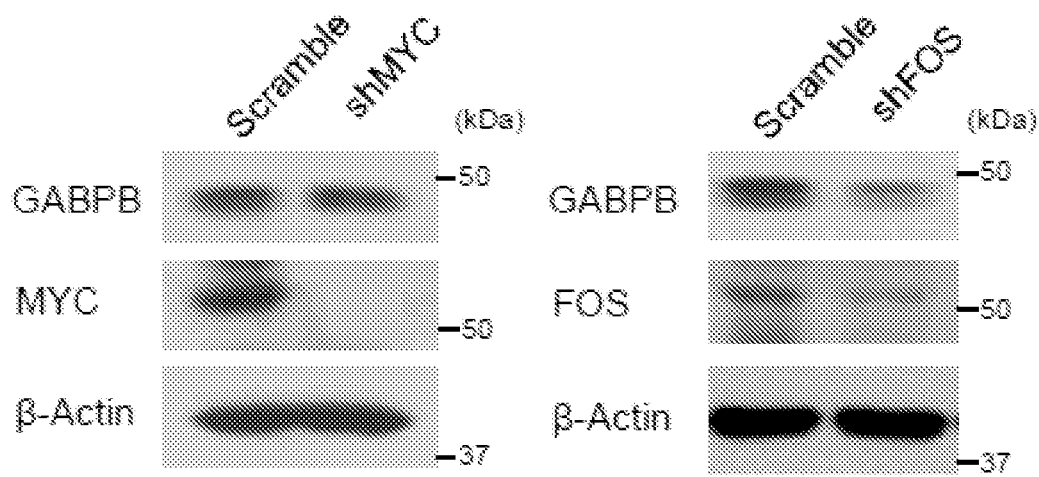
Figure 5E:
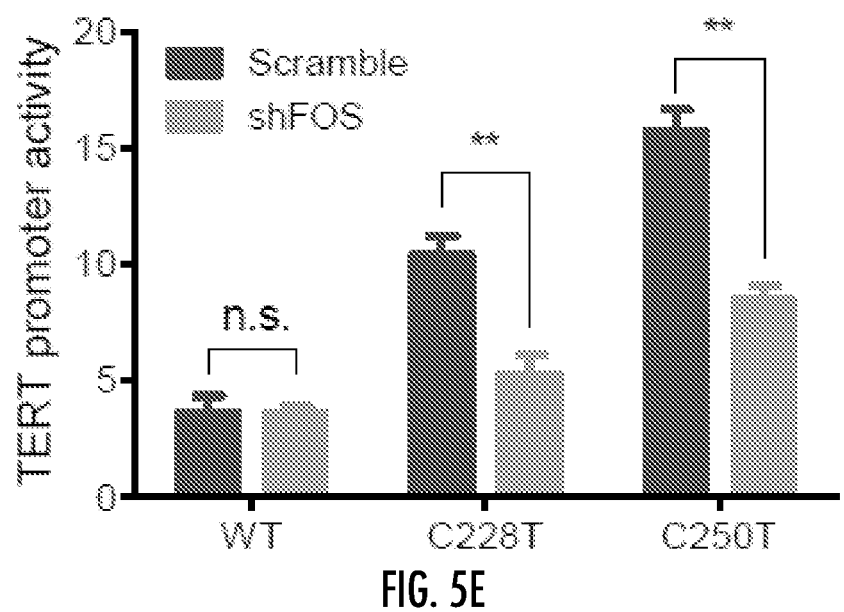
Figure 5F:
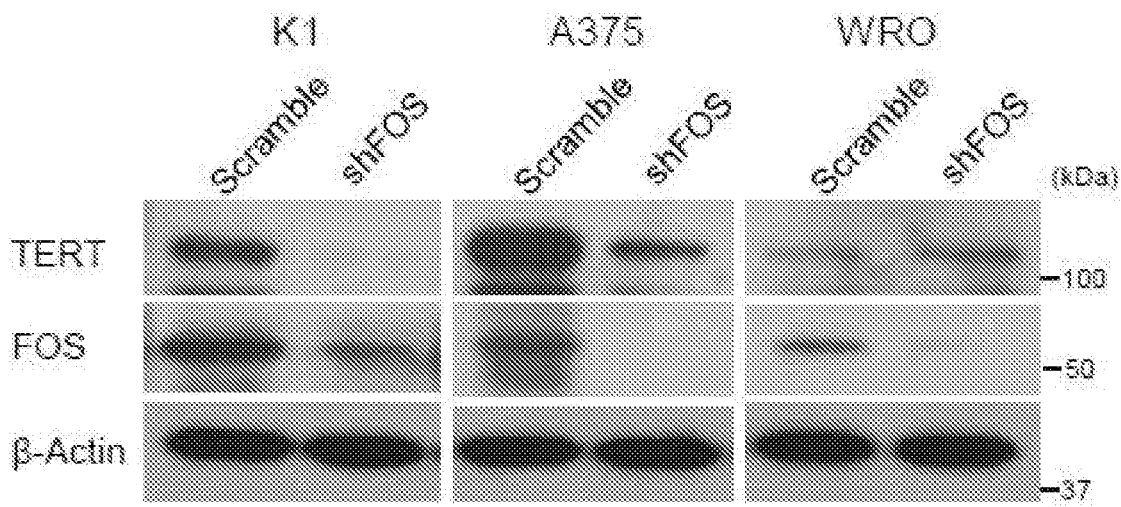

To decipher how BRAF V600E regulated GABPB expression, we took the next step to test our hypothesis that certain target protein molecules of the BRAF/MAPK pathway might function as transcription factors to activate GABPB. Our bioinformatics analyses of the regulatory 5'-untranslated region (5'-UTR) of GABPB revealed that two classical target molecules downstream of the MAPK pathway, FOS and MYC, were predicted to bind to 5'-UTR of GABPB (FIG. 5a). To test this, we constructed a luciferase reporter containing the wild-type 5'-UTR of GABPB and two mutant reporters containing disrupted FOS-binding motif and MYC-binding motif, respectively. If a transcription factor normally binds to the regulatory region and activates a target gene, disruption of the binding site would be expected to lead to decreased activities of the target gene. We found that disruption of the predicted FOS-binding site, but not the MYC-binding site, in the 5'-UTR region of GABPB significantly decreased the reporter activities of the GABPB gene (FIG. 5B), suggesting that FOS, but not MYC, regulated GABPB. We next performed ChIP assay to directly test whether FOS or MYC bound to GABPB in the cell and found that FOS, but not MYC, bound to the 5'-UTR of GABPB (FIG. 5C). We then used specific shRNA to knock down FOS or MYC and found that knockdown of FOS, but not MYC, could decrease the expression of GABPB (FIG. 5D). These results demonstrated that FOS could bind to the 5'-UTR of GABPB and activate its expression. We next examined the role of FOS in TERT expression. Luciferase reporting assay showed that FOS knockdown specifically inhibited the activities of the mutant TERT promoter but not the wild-type TERT promoter (FIG. 5E). Correspondingly, FOS knockdown suppressed TERT expression in cells harboring the TERT promoter mutation, but not in cells harboring the wild-type TERT (FIG. 5F). Taken together, these results demonstrated that FOS was a transcription factor of the GABPB gene, which could directly bind and activate the promoter of GABPB, leading to the upregulation of TERT expression in a TERT promoter mutation-dependent manner.

BRAF V600E Pathway Promoted Phosphorylation and Binding of FOS to GABPB.

Figure 6A:
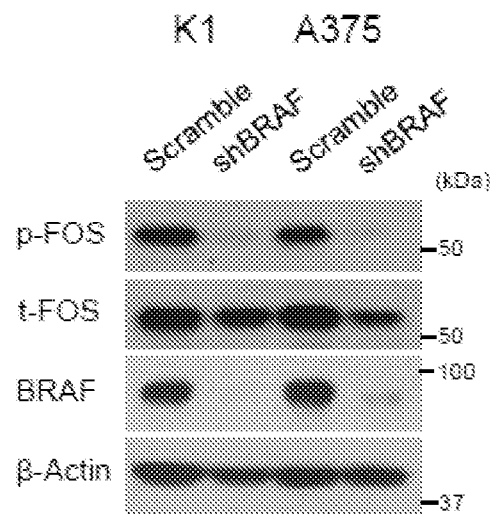
FIG. 6A-6J. BRAF V600E promoted FOS binding to GABPB by upregulating FOS phosphorylation.
Figure 6B:
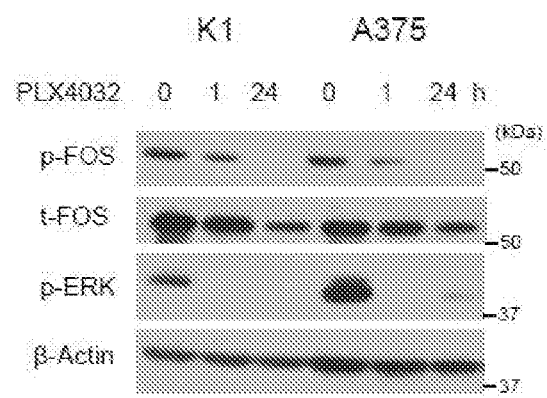
Figure 6C:
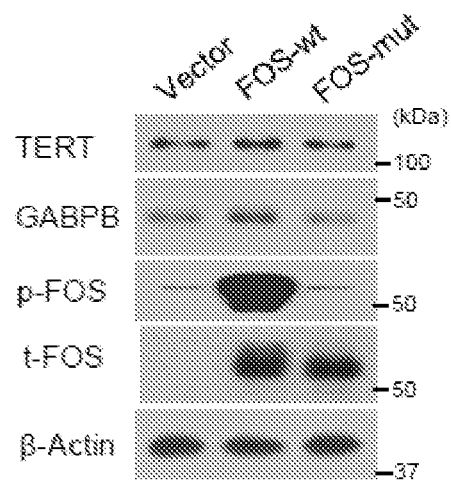
Figure 6D:
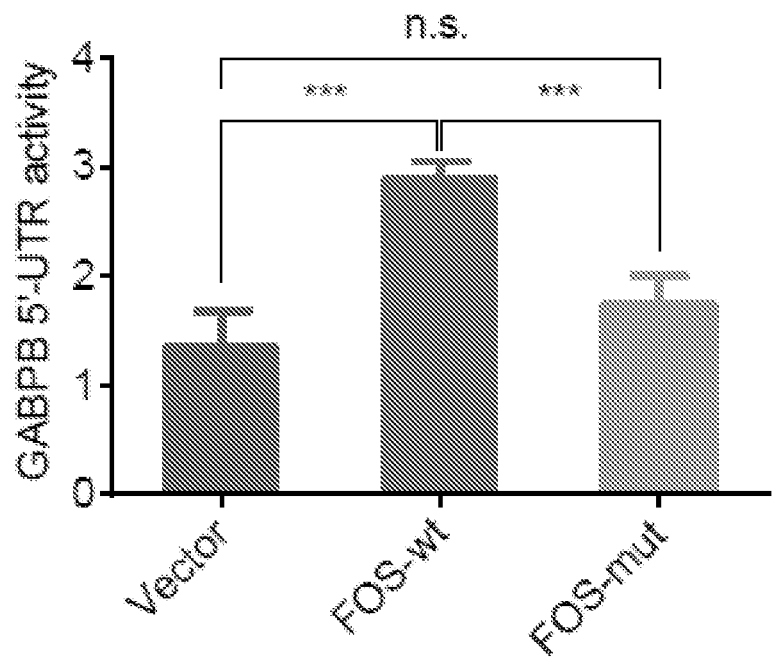
Figure 6E:
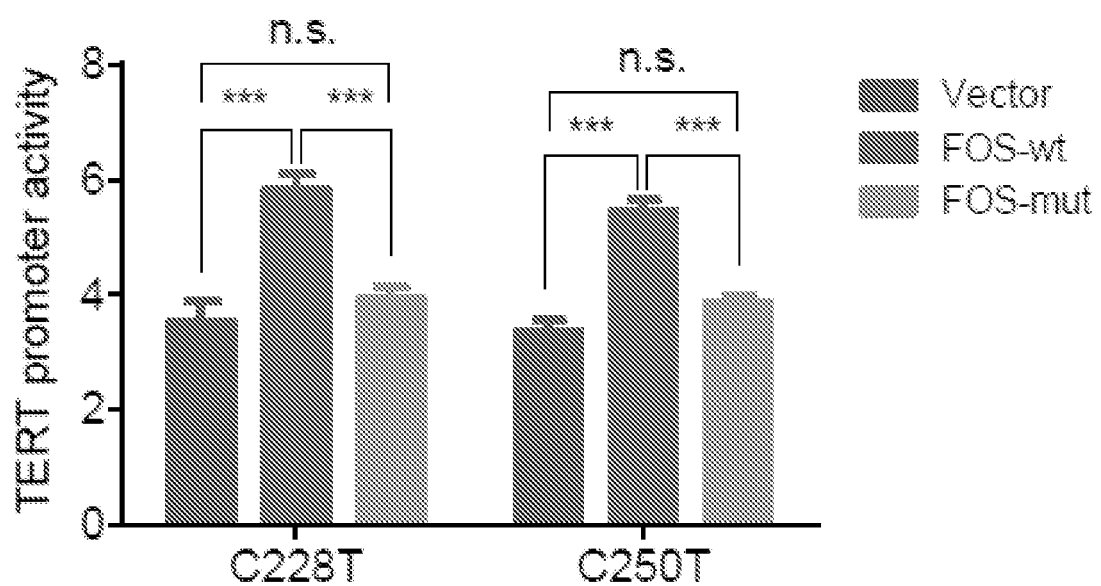
Figure 6F:
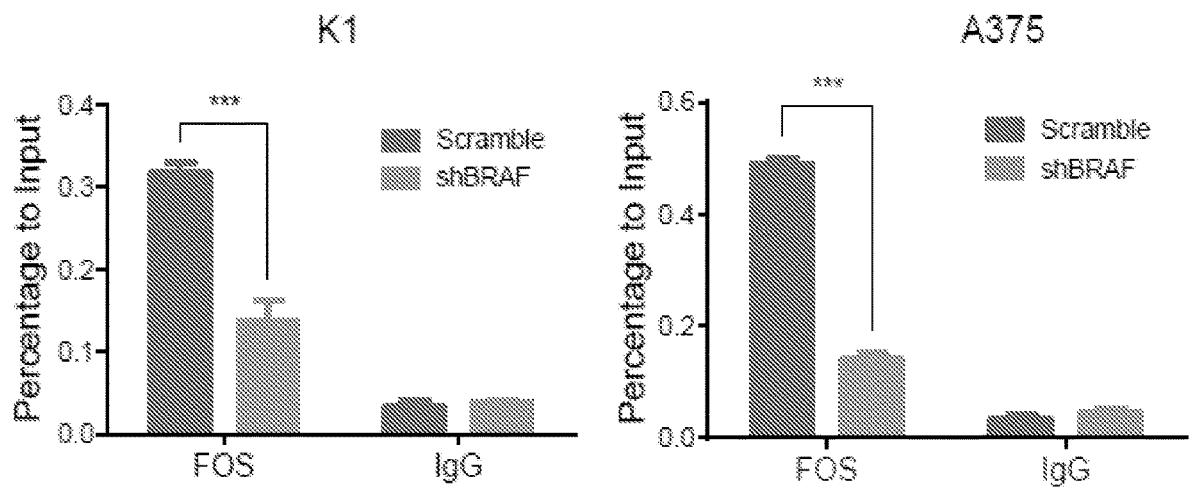
Figure 6G:
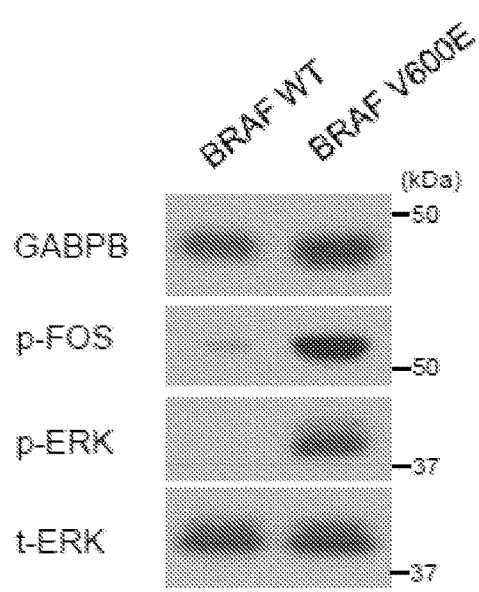
Figure 6H:
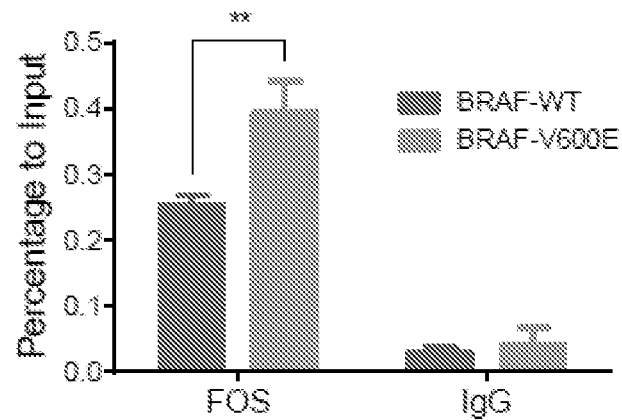
Figure 6I:
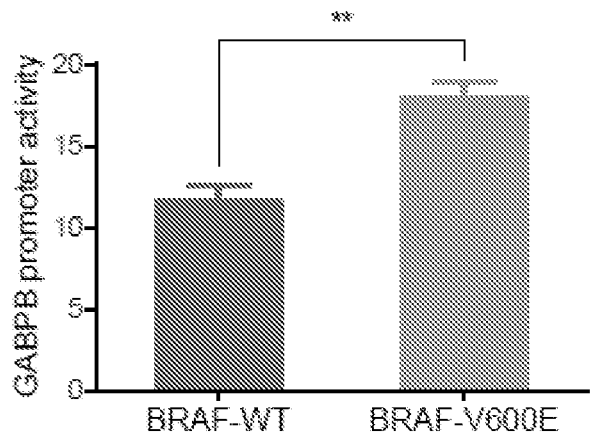
Figure 6J:
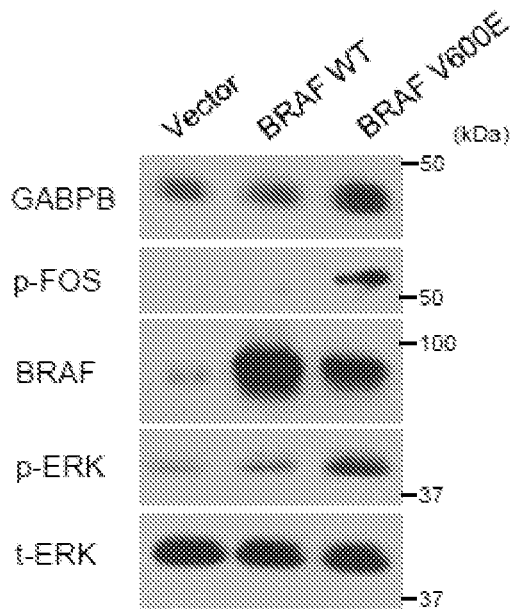

The MAPK pathway was previously shown to stabilize FOS by phosphorylation and stimulate its gene transactivation activities[36, 37]. We therefore investigated the role of BRAF V600E in the phosphorylation of FOS. As shown in FIG. 6A, BRAF knockdown decreased the phosphorylation of FOS in cells harboring BRAF mutation. Similarly, the BRAF V600E-specific inhibitor PLX4032 significantly decreased the phosphorylation of FOS (FIG. 6B). To test the role of BRAF V600E/MAPK pathway-induced FOS phosphorylation in GABPB and mutant TERT activation, we overexpressed the wild-type FOS (FOS-wt) and a mutant FOS (FOS-mut) containing alanine replacements on all the phosphorylation sites (hr-232, Thr-325, Thr-331, and Ser-374) of the target of ERK activation.[38] Overexpression of FOS-wt increased the phosphorylated species of FOS and enhanced the expression of GABPB and TERT (FIG. 6C); it also increased GABPB 5'-UTR and mutant TERT promoter activities (FIG. 6D-6E). In contrast, overexpression of FOS-mut had no effect on GABPB and TERT activities (FIG. 6C-6E). Binding of FOS to GABPB was considerably decreased after BRAF knockdown as demonstrated in ChIP assay (FIG. 6F). Conversely, BRAF V600E mutation knock-in increased the phosphorylation of FOS (FIG. 6G), enhanced its binding to the 5'-UTR of GABPB (FIG. 6H), increased the activities of the GABPB promoter (FIG. 6I), and upregulated the expression of the GABPB gene (FIG. 6G). Similar results were obtained in WRO cells induced to stably express BRAF V600E (FIG. 6J).

Discussion

The unique oncogene duet of coexisting BRAF V600E and TERT promoter mutations is an important recent discovery in human cancer as a robust genetic background for the development of the most aggressive disease in several cancers. For example, it is strongly associated with the most aggressive clinicopathological outcomes of PTC, with hazard ratios for disease recurrence and patient mortality ranging from 30-50 compared with patients harboring neither mutation[24, 27]; PTC-specific mortality nearly exclusively occurred in patients harboring the oncogene duet of BRAF V600E and TERT promoter mutations.[24, 25] Similar robust synergistic role of this oncogene duet in poor clinicopathological outcomes was seen in other human cancers.[22, 23] This genetic duet occurs in about 7-8% PTC[5, 24, 27] and 20-25% melanoma,[9, 22] which correspond to the percentages of the cancer cases with the most aggressive diseases and poorest clinical outcomes. These results suggest that this oncogene duet is a superiorly selected genetic event from an evolutionary perspective. As such, it represents a robust genetic mechanism that underpins aggressive oncogenesis and progression of human cancers and hence ominous clinical outcomes.[39] A fundamental question remains unanswered, however, as to how this oncogene duet cooperates mechanistically, particularly with respect to how BRAF V600E is functionally linked to the mutant TERT, in cooperatively driving human cancer aggressiveness.

Our present study brought insights into the mechanism underlying this synergistic oncogenic operation of BRAF V600E and TERT promoter mutations by demonstrating a robust cooperative role of the two mutations in the expression of TERT, through the BRAF V600E→MAPK pathway→FOS→GABP→TERT axis. Using thyroid cancer and melanoma cells as cancer cell models that harbored BRAF V600E and TERT promoter mutations, we demonstrated that the BRAF V600E/MAPK pathway promoted the formation and binding of transcriptional GABP complex to the mutated TERT promoter and its activation. Specifically, we identified GABPB, the catalytic unit of the GABP complex, but not the DNA binding unit GABPA, as a downstream target gene of the BRAF V600E/MAPK pathway; BRAF V600E-activated MAP kinase pathway strongly upregulated the transcriptional expression of GABPB, thus driving the production of GABP complex, which in turn robustly promoted the expression of TERT. This represents a major progress in understanding the transcriptional machinery of the mutant TERT promoter involving GABP described recently[31, 32] by adding a critical regulatory dimension to it.

To gain further molecular insights, we demonstrated that BRAF/MAPK pathway-phosphorylated FOS plays a critical role in this process by acting as a transcriptional factor of the GABPB gene. As an initial approach to exploring how BRAF V600E regulated GABPB, we performed an in silico analysis, which revealed that both MYC and FOS could bind to the 5'-UTR region of GABPB. Our actual experimental test demonstrated that FOS, but not MYC, could bind to the 5'-UTR of GABPB and activate its expression. We further demonstrated that BRAF V600E/MAPK pathway promoted the phosphorylation of FOS and its binding to the 5'-UTR of GABPB, robustly activating GABPB and the mutant TERT. To directly test if FOS phosphorylation was required for this function of FOS, we engineered FOS to alter the phosphorylation state of FOS and subsequently examined its function in the regulation of GABP and TERT. Compared with the wild-type FOS, phosphorylation-defective FOS lost the ability to activate GABPB and mutant TERT in cancer cells, providing direct evidence that phosphorylation of FOS is required for its regulation of GABPB and mutant TERT. These findings are consistent with the notion that MAPK/ERK pathway-mediated phosphorylation of FOS is required for its transcriptional activity and transformation efficiency.[36, 37, 38, 40] The upregulated GABP transcriptional machinery by the BRAF V600E/MAPK pathway mediated by FOS is expected to promote TERT promoter mutation-dependent TERT expression by facilitating the recruitment and action of classical RNA polymerase. Indeed, this speculation is consistent with a recent study in which RNA polymerase II was found to be recruited to the mutant TERT promoter in response to the stimulation by the MAPK pathway.[41] Interestingly, a recent study showed that GABPA bound to the mutant TERT promoter mediated long-range chromatin interaction and enrichment of active histone marks as a component of the regulatory machinery for TERT transcription.[35]

Unlike GABPB, we demonstrated that MYC could bind to the promoter of TERT and activate it in a TERT promoter mutation-independent manner. This is consistent with the previous finding that MYC bound to the E-box motif in the TERT promoter and upregulated TERT expression.[30] The present study demonstrated that the BRAF V600E/MAPK pathway could also upregulate TERT expression through MYC in a TERT promoter mutation-independent manner, but this was less robust than the TERT promoter mutation-dependent regulation. This provides a mechanism in which BRAF V600E/MAPK pathway can moderately upregulate TERT in cells that do not harbor TERT promoter mutations. Thus, the BRAF V600E/MAPK pathway can upregulate the TERT gene through both TERT promoter mutation-dependent and -independent pathways.

The classical function of TERT is to add telomeres at the end of chromosomes, preventing critical telomere shortening, thus enabling cancer cells acquire replicative immortality.[1] In addition to this function, recent studies have also established TERT as having powerful oncogenic functions in a telomere-independent manner. For example, overexpression of TERT mutant or a naturally occurring alternatively spliced variant of TERT lacking the reverse transcriptase activity stimulated cell proliferation in human and murine cells.[42, 43] In fact, enforced TERT expression in transgenic mice promoted the development of spontaneous tumors.[44, 45] Even expression of a TERT mutant that retained the catalytic activity but was incapable of maintaining telomere length promoted tumor formation in nude mice.[46] Moreover, TERT activated the RNA-dependent RNA polymerase activity,[47] increased cancer cell proliferation by promotes pol III-mediated expression of transfer RNAs[48], and promoted cancer progression by regulating MYC stability and MYC-dependent oncogenesis.[49] The present study similarly demonstrated a robust oncogenic function of TERT and, importantly, its synergism with BRAF V600E in functioning this way.

Figure 7:
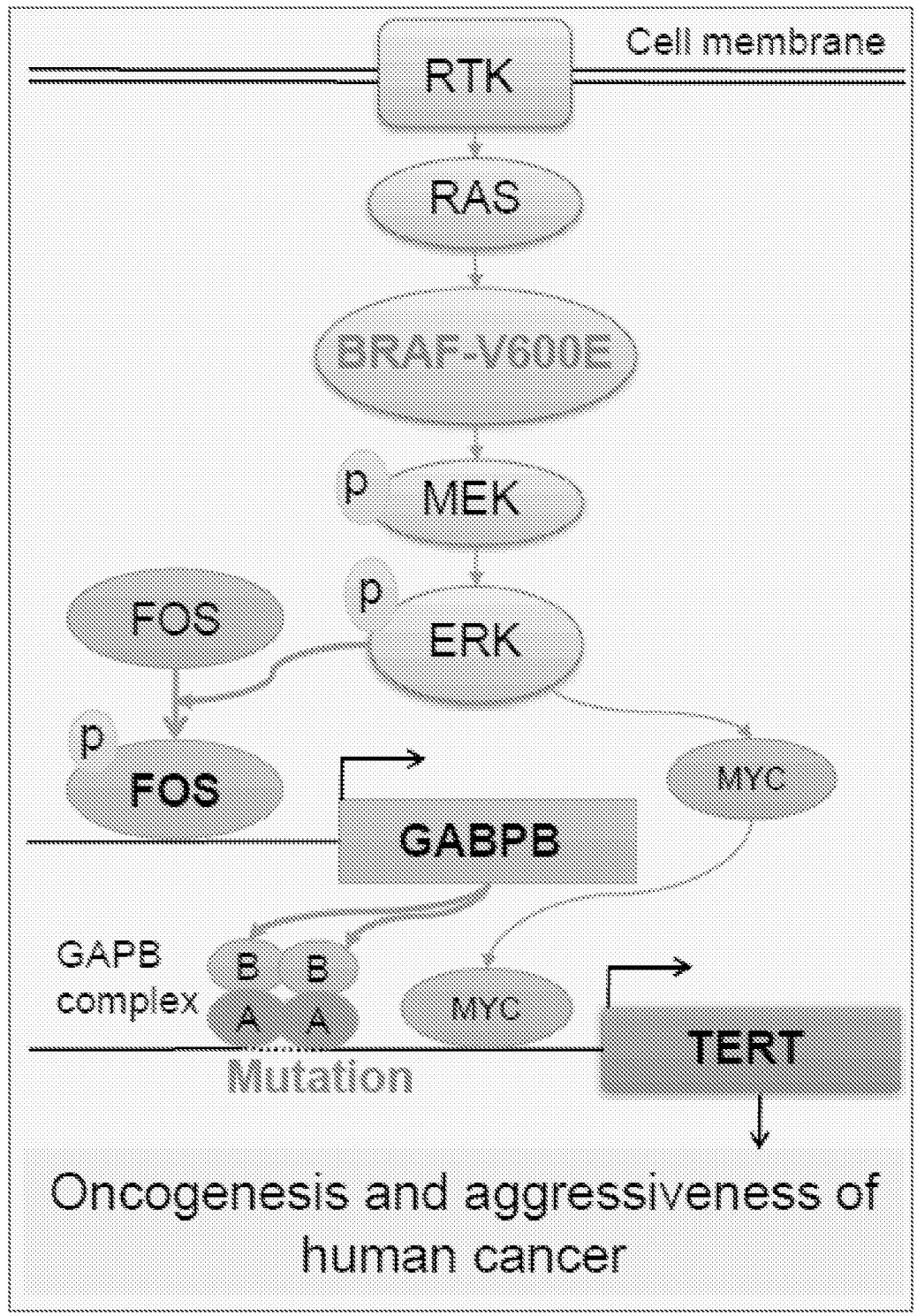
FIG. 7. Oncogenic cooperation of BRAF V600E and TERT promoter mutations. This model illustrates a mechanism for the synergistic oncogenicity between BRAF V600E and TERT promoter mutations in promoting human cancer progression and aggressiveness. This involves promoting TERT expression through the BRAF V600E→MAPK pathway→FOS→GABPB→GABP complex axis for mutant TERT promoter activation; the TERT promoter mutation-independent MYC component promoted by the BRAF V600E/MAPK pathway moderately stimulating TERT expression is also shown.

In summary and as illustrated in FIG. 7, this study demonstrates for the first time that BRAF V600E and TERT promoter mutations cooperatively upregulate TERT expression via the BRAF V600E→MAPK pathway→FOS→GABP→TERT signaling/transcription axis in human cancers. In this process, BRAF V600E/MAP kinase pathway-phosphorylated FOS plays a critical role in oncogenically bridging the BRAF V600E and TERT promoter mutations by acting as a transcriptional factor of the GABPB gene. To a less extent, the BRAF V600E/MAPK pathway also promotes TERT expression via MYC in a TERT promoter mutation-independent manner. The resulting overexpressed TERT has serious oncogenic consequences. This represents a previously unknown molecular mechanism by which the BRAF V600E/MAPK pathway selectively and robustly regulates the mutant TERT, which mechanistically explains the recently observed robust role of the genetic duet of BRAF V600E and TERT promoter mutations in cooperatively promoting the aggressiveness and poor clinical outcomes of several human cancers. This study holds important cancer biological and clinical implications.

REFERENCES

1. Low K C, Tergaonkar V. Telomerase: central regulator of all of the hallmarks of cancer. *Trends Biochem Sci* 38, 426-434 (2013).
2. Horn S. et al. TERT promoter mutations in familial and sporadic melanoma. *Science* 339, 959-961 (2013).
3. Huang F W, Hodis E, Xu M J, Kryukov G V, Chin L, Garraway L A. Highly recurrent TERT promoter mutations in human melanoma. *Science* 339, 957-959 (2013).
4. Killela P J. et al. TERT promoter mutations occur frequently in gliomas and a subset of tumors derived from cells with low rates of self-renewal. *Proc Nad Acad Sci USA* 110, 6021-6026 (2013).
5. Liu R, Xing M. TERT promoter mutations in thyroid cancer. *Endocr Relat Cancer* 23, R143-155 (2016).
6. Liu X, et al. Highly prevalent TERT promoter mutations in aggressive thyroid cancers. *Endocr Relat Cancer* 20, 603-610 (2013).
7. Borah S. et al. TERT promoter mutations and telomerase reactivation in urothelial cancer. *Science* 347, 1006-1010 (2015).
8. Chiba K, Johnson J Z, Vogan J M, Wagner T, Boyle J M, Hockemeyer D. Cancer-associated TERT promoter mutations abrogate telomerase silencing. *Elife* 4, (2015).
9. Heidenreich B. et al. Telomerase reverse transcriptase promoter mutations in primary cutaneous melanoma. *Nat Commun* 5, 3401 (2014).
10. Li C, et al. The C228T mutation of TERT promoter frequently occurs in bladder cancer stem cells and contributes to tumorigenesis of bladder cancer. *Oncotarget* 6, 19542-19551 (2015).

11. Davies H. et al. Mutations of the BRAF gene in human cancer. *Nature* 417, 949-954 (2002).
12. Xing M. BRAF mutation in thyroid cancer. *Endocr Relat Cancer* 12, 245-262 (2005).
13. Xing M. et al. Association between BRAF V600E mutation and recurrence of papillary thyroid cancer. *J Clin Oncol* 33, 42-50 (2015).
14. Xing M. et al. Association between BRAF V600E mutation and mortality in patients with papillary thyroid cancer. *JAMA* 309, 1493-1501 (2013).
15. Safaee Ardekani G, Jafamejad S M, Tan L, Saeedi A, Li G. The prognostic value of BRAF mutation in colorectal cancer and melanoma a systematic review and meta-analysis. *PLoS One* 7, e47054 (2012).
16. Thomas N E et al. Association Between NRAS and BRAF Mutational Status and Melanoma-Specific Survival Among Patients With Higher-Risk Primary Melanoma. *JAMA Oncol* 1, 359-368 (2015).
17. Dahiya S, Haydon D H, Alvarado D, Gurnett C A, Gutmann D H, Leonard J R. BRAF(V600E) mutation is a negative prognosticator in pediatric ganglioglioma. *Acta Neuropathol* 125, 901-910 (2013).
18. Summers M G, Smith C G, Maughan T S, Kaplan R, Escott-Price V, Cheadle J P. BRAF and NRAS Locus-Specific Variants Have Different Outcomes on Survival to Colorectal Cancer. *Clin Cancer Res* 23, 2742-2749 (2017).
19. Griewank K G, et al. TERT promoter mutation status as an independent prognostic factor in cutaneous melanoma. *J Natl Cancer Inst* 106, (2014).
20. Eckel-Passow J E et al. Glioma Groups Based on 1p/19q, IDH, and TERT Promoter Mutations in Tumors. *N Engl J Med* 372, 2499-2508 (2015).
21. Rachakonda P S, et al. TERT promoter mutations in bladder cancer affect patient survival and disease recurrence through modification by a common polymorphism. *Proc Natl Acad Sci USA* 110, 17426-17431 (2013).
22. Macerola E et al. Coexistence of TERT promoter and BRAF mutations in cutaneous melanoma is associated with more clinicopathological features of aggressiveness. *Virchows Arch* 467, 177-184 (2015).
23. Nagore E. et al. TERT promoter mutations in melanoma survival. *Int J Cancer* 139, 75-84 (2016).
24. Liu R, Bishop J, Zhu G, Zhang T, Ladenson P W, Xing M. Mortality Risk Stratification by Combining BRAF V600E and TERT Promoter Mutations in Papillary Thyroid Cancer: Genetic Duet of BRAF and TERT Promoter Mutations in Thyroid Cancer Mortality. *JAMA Oncol* 3, 202-208 (2017).
25. Shen X, Liu R, Xing M. A six-genotype genetic prognostic model for papillary thyroid cancer. *Endocr Relat Cancer* 24, 41-52 (2017).
26. Song Y S. et al. Prognostic effects of TERT promoter mutations are enhanced by coexistence with BRAF or RAS mutations and strengthen the risk prediction by the ATA or TNM staging system in differentiated thyroid cancer patients. *Cancer* 122, 1370-1379 (2016).
27. Xing M. et al. BRAF V600E and TERT promoter mutations cooperatively identify the most aggressive papillary thyroid cancer with highest recurrence. *J Clin Oncol* 32, 2718-2726 (2014).
28. Halaban R et al. PLX4032, a selective BRAF(V600E) kinase inhibitor, activates the ERK pathway and enhances cell migration and proliferation of BRAF melanoma cells. *Pigment Cell Melanoma Res* 23, 190-200 (2010).
29. Joseph E W. et al. The RAF inhibitor PLX4032 inhibits ERK signaling and tumor cell proliferation in a V600E BRAF-selective manner. *Proc Natl Acad Sci USA* 107, 14903-14908 (2010).
30. Wu K J. et al. Direct activation of TERT transcription by c-MYC. *Nat Genet* 21, 220-224 (1999).
31. Bell R J. et al. The transcription factor GABP selectively binds and activates the mutant TERT promoter in cancer. *Science* 348, 1036-1039 (2015).
32. Stem J L, Teodorescu D, Vogelstein B, Papadopoulos N, Cech T R. Mutation of the TERT promoter, switch to active chromatin, and monoallelic TERT expression in multiple cancers. *Genes Dev* 29, 2219-2224 (2015).
33. LaMarco K, Thompson C C, Byers B P, Walton E M, McKnight S L. Identification of Ets- and notch-related subunits in G A binding protein. *Science* 253, 789-792 (1991).
34. Sawada J, Goto M, Sawa C, Watanabe H, Handa H. Transcriptional activation through the tetrameric complex formation of E4TF1 subunits. *EMBO J* 13, 1396-1402 (1994).
35. Akincilar S C, Khattar E, Boon P L, Unal B, Fullwood M J, Tergaonkar V. Long-Range Chromatin Interactions Drive Mutant TERT Promoter Activation. *Cancer Discov* 6, 1276-1291 (2016).
36. Chen R H, Juo P C, Curran T, Blenis J. Phosphorylation of c-Fos at the C-terminus enhances its transforming activity. *Oncogene* 12, 1493-1502 (1996).
37. Okazaki K, Sagata N. The Mos/MAP kinase pathway stabilizes c-Fos by phosphorylation and augments its transforming activity in NIH 3T3 cells. *EMBO J* 14, 5048-5059 (1995).
38. Monje P, Marinissen M J, Gutkind J S. Phosphorylation of the carboxyl-terminal transactivation domain of c-Fos by extracellular signal-regulated kinase mediates the transcriptional activation of AP-1 and cellular transformation induced by platelet-derived growth factor. *Mol Cell Biol* 23, 7030-7043 (2003).
39. Ngeow J, Eng C. TERT and BRAF in thyroid cancer: teaming up for trouble. *J Clin Oncol* 32, 2683-2684 (2014).
40. Monje P, Hemandez-Losa J, Lyons R J, Castellone M D, Gutkind J S. Regulation of the transcriptional activity of c-Fos by ERK. A novel role for the prolyl isomerase PIN1. *J Biol Chem* 280, 35081-35084 (2005).
41. Li Y, Cheng H S, Chng W J, Tergaonkar V. Activation of mutant TERT promoter by RAS-ERK signaling is a key step in malignant progression of BRAF-mutant human melanomas. *Proc Natl Acad Sci USA* 113, 14402-14407 (2016).
42. Choi J. et al. TERT promotes epithelial proliferation through transcriptional control of a Myc- and Wnt-related developmental program. *PLoS Genet* 4, e10 (2008).
43. Hrdlickova R, Nehyba J, Bose H R, Jr. Alternatively spliced telomerase reverse transcriptase variants lacking telomerase activity stimulate cell proliferation. *Mol Cell Biol* 32, 4283-4296 (2012).
44. Artandi S E, et al. Constitutive telomerase expression promotes mammary carcinomas in aging mice. *Proc Natl Acad Sci USA* 99, 8191-8196 (2002).
45. Gonzalez-Suarez E, et al. Increased epidermal tumors and increased skin wound healing in transgenic mice overexpressing the catalytic subunit of telomerase, mTERT, in basal keratinocytes. *EMBO J* 20, 2619-2630 (2001).

46. Stewart S A, et al. Telomerase contributes to tumorigenesis by a telomere length-independent mechanism. *Proc Nad Acad Sci USA* 99, 12606-12611 (2002).
47. Maida Y. et al. An RNA-dependent RNA polymerase formed by TERT and the RMRP RNA. *Nature* 461, 230-235 (2009).
48. Khattar E. et al. Telomerase reverse transcriptase promotes cancer cell proliferation by augmenting tRNA expression. *J Clin Invest* 126, 4045-4060 (2016).
49. Koh C M, et al. Telomerase regulates MYC-driven oncogenesis independent of its reverse transcriptase activity. *J Clin Invest* 125, 2109-2122 (2015).
50. Liu D, Hou P, Liu Z, Wu G, Xing M. Genetic alterations in the phosphoinositide 3-kinase/Akt signaling pathway confer sensitivity of thyroid cancer cells to therapeutic targeting of Akt and mammalian target of rapamycin. *Cancer Res* 69, 7311-7319 (2009).
51. Liu D, Liu X, Xing M. Activities of multiple cancer-related pathways are associated with BRAF mutation and predict the resistance to BRAF/MEK inhibitors in melanoma cells. Cell Cycle 13, 208-219 (2014).
52. Xing M. et al. BRAF mutation predicts a poorer clinical prognosis for papillary thyroid cancer. *J Clin Endocrinol Metab* 90, 6373-6379 (2005).
53. Livak K J, Schmittgen T D. Analysis of relative gene expression data using real-time quantitative PCR and the 2(-Delta Delta C(T)) Method. *Methods* 25, 402-408 (2001).
54. Murugan A K, Alzahrani A, Xing M. Mutations in critical domains confer the human mTOR gene strong tumorigenicity. *J Biol Chem* 288, 6511-6521 (2013).
55. Hou P, Liu D, Xing M. Genome-wide alterations in gene methylation by the BRAF V600E mutation in papillary thyroid cancer cells. *Endocr Relat Cancer* 18, 687-697 (2011).
56. Boehm J S et al. Integrative genomic approaches identify IKBKE as a breast cancer oncogene. *Cell* 129, 1065-1079 (2007).
57. Nelson J D, Denisenko O, Bomsztyk K. Protocol for the fast chromatin immunoprecipitation (ChIP) method. *Nat Protoc* 1, 179-185 (2006).
58. Liu D, Liu Z, Condouris S, Xing M. BRAF V600E maintains proliferation, transformation, and tumorigenicity of BRAF-mutant papillary thyroid cancer cells. *J Clin Endocrinol Metab* 92, 2264-2271 (2007).
59. Tomayko M M, Reynolds C P. Determination of subcutaneous tumor size in athymic (nude) mice. *Cancer Chemother Pharmacol* 24, 148-154 (1989).

---

We claim:

1. A method for identifying a subject having thyroid cancer as being treatable with a FOS inhibitor comprising the steps of
   (a) detecting a C228T and/or C250T mutation TERT promoter mutation in the genome of the subject;
   (b) detecting a BRAF V600E mutation in the genome of the subject; and
   (c) administering a FOS inhibitor to the subject, wherein a subject having both a TERT mutation and a BRAF mutation will respond to FOS inhibitor treatment.

2. The method of claim 1, wherein the FOS inhibitor comprises a benzophenone derivative.

3. The method of claim 2 wherein the benzophenone derivative comprises 3-{5-[4-(cyclopentyloxy)-2-hydroxy-benzoyl]-2-[(3-hydroxyl-1,2-benzisoxazo-1-6-yl)methoxy}phenyl}propanoic acid (T-5224).

4. The method of claim 2, wherein the benzophenone derivative is selected from the group consisting of: 3-{5-[4-(cyclopentyloxy)-2-hydroxybenzoyl]-2-[(3-hydroxyl-1,2-benzisoxazo-1-6-yl)methoxy}phenyl}propanoic acid; 2-(4-morpholinyl)ethyl 3-{5-[4-(cyclopentyloxy)-2-hydroxybenzoyl]-2-[(3-hydroxy-1,2-benzisoxazol--6-yl) methoxy]phenyl}propanoate; 4-({2-(2-carboxyethyl)-4-[4-(cyclopentyloxy)-2-hydroxybenzoyl]phenoxy}met-hyl) benzoic acid; and 3-(5-[4-(cyclopentyloxy)-2-hydroxybenzoyl]-2-{[4-(3-hydroxy-5-isoxazolyl)-benzyl] oxy}phenyl)propanoic acid.

5. The method of claim 1, wherein the FOS inhibitor comprise a derivative of retinoic acid.

6. The method of claim 5, wherein the derivative of retinoic acid comprises (2E,z1E,6Z,8E)-3-methyl-7-(4-methylphenyl)-9-(2,6,6-trimethylcyclohexen-1-yl)-2,4,6,8-nonatetraenoic acid (SR11302).

7. The method of claim 5, wherein the derivative of retinoic acid is selected from the group consisting of: (2E,4E,6Z,8E)-3-methyl-7-(4-methylphenyl)-9-(2,6,6-trimethylcyclohexen-1-yl)-2,4,6,8-nonatetraenoic acid (SR11302); (2-(3,4-dihydro-4,4-dimethyl-2H-1-benzopyran-6-yl)-2-(4-carboxyphenyl)-1,3-dithiane (SR11238); (E)-4-(2-(5,6,7,8-tetrahydro-5,5,8,8-tetramethyl-2-naphthalenyl)-3-phenylpropenyl)benzoic acid (SR11327); methyl (Z)-4-(1-acetoxy-2-(5,6,7,8-tetrahydro-5,5,8,8-tetramethyl-2-naphthalenyl)ethenyl)benzoate (SR11220) and 5-((5,6,7,8-tetrahydro-5,5,8,8-tetramethyl-2-naphthalenyl)carbonyl)-2-naphthatenecarboxylic acid (SR11228).

8. The method of claim 1, wherein the FOS inhibitor comprises curcumin, difluorinated curcumin (DFC) or dihydroguaiaretic acid (DHGA).

9. The method of claim 1, further comprising the step of administering a TERT inhibitor to the subject.

10. The method of claim 9, wherein the TERT inhibitor comprises 2-[(E)-3-naphthen-2-yl but-2-enoylamino]benzoic acid (BIBR1532) and derivatives thereof.

11. The method of claim 1, further comprising the steps of:
(d) administering a BRAF inhibitor to the subject.

12. The method of claim 11, wherein the BRAF inhibitor is selected from the group consisting of vemurafenib, dabrafenib, encorafenib and derivatives of the foregoing.

13. The method of claim 11, further comprising the step of administering a MEK inhibitor to the subject.

14. The method of claim 13, wherein the MEK inhibitor is selected from the group consisting of selumetinib, cobimetinib, binimetinib, trametinib and derivatives of the foregoing.

* * * * *